(12) United States Patent
Favaloro et al.

(10) Patent No.: US 11,708,418 B2
(45) Date of Patent: Jul. 25, 2023

(54) COMPOSITIONS, METHODS AND/OR KITS COMPRISING A RECOMBINANT HUMAN CD38- EXTRACELLULAR DOMAIN

(71) Applicant: GRIFOLS DIAGNOSTIC SOLUTIONS INC., Emeryville, CA (US)

(72) Inventors: Vincenzo Favaloro, San Francisco, CA (US); Matteo Binda, Ecuvillens (CH); John A. Hall, Rohnert Park, CA (US); Elizabeth Booth, Berkeley, CA (US); Jody Berry, Easton, PA (US); Peter Schwind, Fribourg (CH)

(73) Assignee: GRIFOLS DIAGNOSTIC SOLUTIONS INC., Emeryville, CA (US)

( * ) Notice: Subject to any disclaimer, the term of this patent is extended or adjusted under 35 U.S.C. 154(b) by 0 days.

(21) Appl. No.: 16/079,068

(22) PCT Filed: Jun. 1, 2018

(86) PCT No.: PCT/IB2018/053939
§ 371 (c)(1),
(2) Date: Aug. 22, 2018

(87) PCT Pub. No.: WO2019/030581
PCT Pub. Date: Feb. 14, 2019

(65) Prior Publication Data
US 2021/0198376 A1    Jul. 1, 2021

Related U.S. Application Data

(60) Provisional application No. 62/543,788, filed on Aug. 10, 2017.

(51) Int. Cl.
| | | |
|---|---|---|
| *G01N 33/53* | (2006.01) | |
| *C07K 14/52* | (2006.01) | |
| *C07K 16/28* | (2006.01) | |
| *G01N 33/80* | (2006.01) | |

(52) U.S. Cl.
CPC ........ *C07K 16/2896* (2013.01); *G01N 33/80* (2013.01); *C07K 2319/21* (2013.01); *C07K 2319/24* (2013.01); *C07K 2319/30* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 9,777,063 B2 * | 10/2017 | Freiberg | .................. | A61K 45/06 |
| 10,584,167 B2 * | 3/2020 | Willuda | .................. | A61P 35/00 |
| 2002/0102250 A1 * | 8/2002 | Deibel, Jr. | .................. | C12Q 1/34 |
| | | | | 435/220 |
| 2013/0029358 A1 * | 1/2013 | Valmori | ............ | G01N 33/56972 |
| | | | | 530/300 |
| 2014/0112924 A1 * | 4/2014 | Lazar | ...................... | A61P 19/02 |
| | | | | 424/134.1 |
| 2015/0231235 A1 * | 8/2015 | Van De Winkel | ..... | A61K 31/69 |
| | | | | 424/139.1 |
| 2015/0355172 A1 * | 12/2015 | Kraus | ............... | G01N 33/57484 |
| | | | | 435/320.1 |
| 2016/0200828 A1 * | 7/2016 | Tesar | ................... | C12N 9/2497 |
| | | | | 424/139.1 |
| 2016/0271243 A1 * | 9/2016 | Rao | ....................... | A61K 9/7023 |
| 2016/0304973 A1 * | 10/2016 | Chiorazzi | ......... | G01N 33/57426 |
| 2018/0021429 A1 * | 1/2018 | Kudo | ...................... | A61P 37/04 |
| | | | | 424/133.1 |

FOREIGN PATENT DOCUMENTS

| | | | | |
|---|---|---|---|---|
| WO | WO 2010/037835 A2 | 4/2010 | | |
| WO | WO 2010/037835 A3 | 4/2010 | | |
| WO | WO 2010/037837 A2 | 4/2010 | | |
| WO | WO 2010/037837 A3 | 4/2010 | | |
| WO | WO 2016/071355 A1 | 5/2016 | | |
| WO | WO-2017081211 A2 * | 5/2017 | ................ | A61P 1/04 |

OTHER PUBLICATIONS

Ansari, Mohd Ziauddin. Why do we mostly use only 6xHis Tag to purify proteins not 8xHis or 10xHis? ResearchGate, 2014, p. 1. (Year: 2014).*
Rui et al. PECAM-1 Ligation Negatively Regulates TLR4 Signaling in Macrophages. J Immunol 2007; 179:7344-7351. (Year: 2007).*
Ishida et al. The Trifunctional Antibody (tri-31C2) Targeting CD38 and CD3 Has a Stronger Anti-Myeloma Effect Than the Chimeric Anti-CD38 Monoclonal Antibody (ch-31C2). Blood, (Dec. 2, 2016) vol. 128, No. 22, p. 2097 (Year: 2016).*
Wykes et al. Dendritic cells and follicular dendritic cells express a novel ligand for CD38 which influences their maturation and antibody responses. Immunology 2004, 113:218-327. (Year: 2004).*
Catalan et al. Dendritic cells express possible ligand(s) for CD38. Journal of Immunology, 186(1). Abstract No. 45.13 (Year: 2011).*
Kobayashi et al. Plasmodium falciparum BAEBL Binds to Heparan Sulfate Proteoglycans on the Human Erythrocyte Surface. JBC, 285(3):1716-1725, 2010. (Year: 2010).*
Genbank Accession No. P28907.2. Full=ADP-ribosyl cyclase/cyclic ADP-ribose hydrolase 1; AltNa—Protein—NCBI. 2014., 1-8. (Year: 2014).*

(Continued)

*Primary Examiner* — Maher M Haddad
(74) *Attorney, Agent, or Firm* — Knobbe, Martens, Olson & Bear LLP

(57) ABSTRACT

A composition that binds to an anti-CD38 antibody includes a specific sequence of a recombinant soluble form of an extracellular domain of CD38 and/or a fragment thereof that interferes with binding activity of the anti-CD38 antibody. The composition can be included in a kit for bio-monitoring research and diagnostic assays. The composition can be used to neutralize an anti-CD38 antibody in a sample and/or to select a suitable red blood cell unit for a patient treated with anti-CD38 antibodies.

24 Claims, 17 Drawing Sheets
Specification includes a Sequence Listing.

(56) References Cited

OTHER PUBLICATIONS

AABB, Mitigating the Anti-CD38 Interference with Serologic Testing. Jan. 15, 2016. pages 1-4 (Year: 2016).*
Bell et al. To fuse or not to fuse: What is your purpose? Protein Science 2013 vol. 22:1466-1477 (Year: 2013).*
Chapuy et al. Resolving the daratumumab interference with blood compatibility testing. Transfusion, 55:15451554, 2015 (Year: 2015).*
Recombinant Human CD38 Fc Chimera Protein, CF 10920-AC-020: R&D Systems, Oct. 25, 2022. pp. 1-12 (Year: 2022).*
Chimerigen Laboratories, CHI-HF-211CD38. CD38 (human):Fc (mouse) (rec.) . Oct. 24, 2022, p. 1-2 (Year: 2022).*
Van de Donk et al. Monoclonal antibodies targeting CD38 in hematological malignancies and beyond. Immunological Reviews 2016 vol. 270: 95-112. (Year: 2016).*
Aricescu et al., A time- and cost-efficient system for high-level protein production in mammalian cells, Acta Crystallographica, vol. D62, pp. 1243-1250, 2006.
Bruzzone et al., Dimeric and tetrameric forms of catalytically active transmembrane CD38 in transfected HeLa cells, FEBS Letters, vol. 433, pp. 275-278, 1998.
Chapuy et al., Resolving the daratumumab interference with blood compatibility testing, Transfusion, vol. 55, pp. 1545-1554, 2015.
Chapuy et al., International validation of a dithiothreitol (DTT)-based method to resolve the daratumumab interference with blood compatibility testing, Transfusion, vol. 56, pp. 2964-2972, 2016.
Lokhorst et al., Targeting CD38 with Daratumumab monotherapy in multiple myeloma, The New England Journal of Medicine, vol. 373, pp. 1207-1219, 2015.
Van De Donk et al., Monoclonal antibodies targeting CD38 in hematological malignancies and beyond, Immunological Reviews, vol. 270, pp. 95-112, 2016.
De Weers, M., et al., Daratumumab, a Novel Therapeutic Human CD38 Monoclonal Antibody, Induces Killing of Multiple Myeloma and Other Hematological Tumors, The Journal of Immunology, vol. 186, pp. 1840-1848, 2010.

Deckert, J., et al., SAR650984, A Novel Humanized CD38-Targeting Antibody, Demonstrates Potent Antitumor Activity in Models of Multiple Myeloma and Other CD38+ Hematologic Malignancies, Clinical Cancer Research, vol. 20, No. 17, pp. 4574-4583, 2014.
International Search Report & Written Opinion, dated Oct. 25, 2018 in International Patent Application No. PCT/IB2018/053939.
Khoo, K.M., et al., Expression and purification of the recombinant His-tagged GST-CD38 fusion protein using the baculovirus/insect cell expression system, Protein Expression and Purification, vol. 40, pp. 396-403, 2005.
Kukimoto, I., et al., Stimulation of ADP-Ribosyl Cyclase Activity of the Cell Surface Antigen CD38 by Zinc Ions Resulting from Inhibition of Its NAD+ Glycohydrolase Activity, European Journal of Biochemistry, vol. 239, pp. 177-182, 1996.
Mekhaiel, D.N.A., et al., Polymeric human Fc-fusion proteins with modified effector functions, Scientific Reports, vol. 1, pp. 1-11, 2011.
Oostendorp, M., et al., When blood transfusion medicine becomes complicated due to interference by monoclonal antibody therapy, Transfusion, vol. 55, pp. 1555-1562, 2015.
Radu Aricescu, A., et al., A time- and cost-efficient system for high-level protein production in mammalian cells, ACTA Crystallographica Section D Biological Crystallography, vol. D62, pp. 1243-1250, 2006.
Raran-Kurussi, S., et al., Positional effects of fusion partners on the yield and solubility of MBP fusion proteins, Protein Expression and Purification, vol. 110, pp. 159-164, 2015.
Salinas, N.D., et al., Critical Glycosylated Residues in Exon Three of Erythrocyte Glycophorin A Engage Plasmodium falciparum EBA-175 and Define Receptor Specificity, MBIO, vol. 5, No. 5, e01606-14, pp. 1-10, 2014.
Tohgo, A., et al., Lysine 129 of CD38 (ADP-ribosyl Cyclase/Cyclic ADP-ribose Hydrolase) Participates in the Binding of ATP to Inhibit the Cyclic ADP-ribose Hydrolase, Journal of Biological Chemistry, vol. 272, No. 7, pp. 3879-3882, 1997.

* cited by examiner

FIG. 2

VDRWRQQWSGPGTTKRFPETVLARCVKYTEIHPEMRHV
DCQSVWDAFKGAFISKHPCNITEEDYQPLMKLGTQTVPC
NKILLWSRIKDLAHQFTQVQRDMFTLEDTLLGYLADDLT
WCGEFNTSKINYQSCPDWRKDCSNNPVSVFWKTVSRRF
AEAACDVVHVMLNGSRSKIFDKNSTFGSVEVHNLQPEK
VQTLEAWVIHGGREDSRDLCQDPTIKELESIISKRNIQFSC
KNIYRPDKFLQCVKNPEDSSCTSEIGIHHHHHHHHHH (SEQ ID NO: 8)

FIG. 6

PRWRQQWSGPGTTKRFPETVLARCVKYTEIHPEMRHVD
CQSVWDAFKGAFISKHPCNITEEDYQPLMKLGTQTVPCN
KILLWSRIKDLAHQFTQVQRDMFTLEDTLLGYLADDLTW
CGEFNTSKINYQSCPDWRKDCSNNPVSVFWKTVSRRFAE
AACDVVHVMLNGSRSKIFDKNSTFGSVEVHNLQPEKVQ
TLEAWVIHGGREDSRDLCQDPTIKELESIISKRNIQFSCKNI
YRPDKFLQCVKNPEDSSCTSEI (SEQ ID NO: 1)

FIG. 7

LQPEKVQTLEAWVIHGGREDSRDLCQDPTIKELESIISKRN
IQFSCKNIYR (SEQ ID NO: 2)

FIG. 8

VQTLEAWVIHGG (SEQ ID NO: 3)

FIG. 9

SKRNIQFSCKNIYR (SEQ ID NO: 4)

FIG. 10

HGVPRDCGCKPCICTVPEVSSVFIFPPKPKDVLTITLTPKV
TCVVVDISKDDPEVQFSWFVDDVEVHTAQTQPREEQFNS
TFRSVSELPIMHQDWLNGKEFKCRVNSAAFPAPIEKTISK
TKGRPKAPQVYTIPPPKEQMAKDKVSLTCMITDFFPEDIT
VEWQWNGQPAENYKNTQPIMDTDGSYFVYSKLNVQKS
NWEAGNTFTCSVLHEGLHNHHTEKSLSHSPGIHHHHHHH
HHH (SEQ ID NO: 5)

FIG. 11

MHHHHHHHHHHGSKTEEGKLVIWINGDKGYNGLAEVG
KKFEKDTGIKVTVEHPDKLEEKFPQVAATGDGPDIIFWA
HDRFGGYAQSGLLAEITPDKAFQDKLYPFTWDAVRYNG
KLIAYPIAVEALSLIYNKDLLPNPPKTWEEIPALDKELKAK
GKSALMFNLQEPYFTWPLIAADGGYAFKYENGKYDIKD
VGVDNAGAKAGLTFLVDLIKNKHMNADTDYSIAEAAFN
KGETAMTINGPWAWSNIDTSKVNYGVTVLPTFKGQPSKP
FVGVLSAGINAASPNKELAKEFLENYLLTDEGLEAVNKD
KPLGAVALKSYEEELAKDPRIAATMENAQKGEIMPNIPQ
MSAFWYAVRTAVINAASGRQTVDEALKDAQTNSSSGEN
LYFQGT (SEQ ID NO: 6)

FIG. 13

SEQUENCE LISTING

<160> NUMBER OF SEQ ID NOS: 30

<210> SEQ ID NO 1
<211> LENGTH: 257
<212> TYPE: PRT
<213> ORGANISM: Artificial Sequence
<220> FEATURE:
<223> OTHER INFORMATION: Synthetic; CD38 extra-cellular domain (CD38ecd)

<400> SEQUENCE: 1

Pro Arg Trp Arg Gln Gln Trp Ser Gly Pro Gly Thr Thr Lys Arg Phe
1               5                   10                  15

Pro Glu Thr Val Leu Ala Arg Cys Val Lys Tyr Thr Glu Ile His Pro

```
                     20                  25                  30
Glu Met Arg His Val Asp Cys Gln Ser Val Trp Asp Ala Phe Lys Gly
             35                  40                  45
Ala Phe Ile Ser Lys His Pro Cys Asn Ile Thr Glu Glu Asp Tyr Gln
         50                  55                  60
Pro Leu Met Lys Leu Gly Thr Gln Thr Val Pro Cys Asn Lys Ile Leu
 65                  70                  75                  80
Leu Trp Ser Arg Ile Lys Asp Leu Ala His Gln Phe Thr Gln Val Gln
                 85                  90                  95
Arg Asp Met Phe Thr Leu Glu Asp Thr Leu Leu Gly Tyr Leu Ala Asp
             100                 105                 110
Asp Leu Thr Trp Cys Gly Glu Phe Asn Thr Ser Lys Ile Asn Tyr Gln
         115                 120                 125
Ser Cys Pro Asp Trp Arg Lys Asp Cys Ser Asn Asn Pro Val Ser Val
     130                 135                 140
Phe Trp Lys Thr Val Ser Arg Arg Phe Ala Glu Ala Ala Cys Asp Val
145                 150                 155                 160
Val His Val Met Leu Asn Gly Ser Arg Ser Lys Ile Phe Asp Lys Asn
                 165                 170                 175
Ser Thr Phe Gly Ser Val Glu Val His Asn Leu Gln Pro Glu Lys Val
             180                 185                 190
Gln Thr Leu Glu Ala Trp Val Ile His Gly Gly Arg Glu Asp Ser Arg
         195                 200                 205
Asp Leu Cys Gln Asp Pro Thr Ile Lys Glu Leu Glu Ser Ile Ile Ser
     210                 215                 220
Lys Arg Asn Ile Gln Phe Ser Cys Lys Asn Ile Tyr Arg Pro Asp Lys
225                 230                 235                 240
Phe Leu Gln Cys Val Lys Asn Pro Glu Asp Ser Ser Cys Thr Ser Glu
                 245                 250                 255
Ile

<210> SEQ ID NO 2
<211> LENGTH: 51
<212> TYPE: PRT
<213> ORGANISM: Artificial Sequence
<220> FEATURE:
<223> OTHER INFORMATION: Synthetic; DARA epitopes

<400> SEQUENCE: 2

Leu Gln Pro Glu Lys Val Gln Thr Leu Glu Ala Trp Val Ile His Gly
 1               5                  10                  15

Gly Arg Glu Asp Ser Arg Asp Leu Cys Gln Asp Pro Thr Ile Lys Glu
                 20                  25                  30

Leu Glu Ser Ile Ile Ser Lys Arg Asn Ile Gln Phe Ser Cys Lys Asn
             35                  40                  45

Ile Tyr Arg
     50

<210> SEQ ID NO 3
<211> LENGTH: 12
<212> TYPE: PRT
<213> ORGANISM: Artificial Sequence
<220> FEATURE:
<223> OTHER INFORMATION: Synthetic; DARA epitopes

<400> SEQUENCE: 3

Val Gln Thr Leu Glu Ala Trp Val Ile His Gly Gly
```

-continued

```
1               5                   10
```

<210> SEQ ID NO 4
<211> LENGTH: 14
<212> TYPE: PRT
<213> ORGANISM: Artificial Sequence
<220> FEATURE:
<223> OTHER INFORMATION: Synthetic; DARA epitopes

<400> SEQUENCE: 4

```
Ser Lys Arg Asn Ile Gln Phe Ser Cys Lys Asn Ile Tyr Arg
1               5                   10
```

<210> SEQ ID NO 5
<211> LENGTH: 239
<212> TYPE: PRT
<213> ORGANISM: Artificial Sequence
<220> FEATURE:
<223> OTHER INFORMATION: Synthetic; Mouse Fc-10H

<400> SEQUENCE: 5

```
His Gly Val Pro Arg Asp Cys Gly Cys Lys Pro Cys Ile Cys Thr Val
1               5                   10                  15

Pro Glu Val Ser Ser Val Phe Ile Phe Pro Pro Lys Pro Lys Asp Val
                20                  25                  30

Leu Thr Ile Thr Leu Thr Pro Lys Val Thr Cys Val Val Val Asp Ile
            35                  40                  45

Ser Lys Asp Asp Pro Glu Val Gln Phe Ser Trp Phe Val Asp Asp Val
        50                  55                  60

Glu Val His Thr Ala Gln Thr Gln Pro Arg Glu Gln Phe Asn Ser
65                  70                  75                  80

Thr Phe Arg Ser Val Ser Glu Leu Pro Ile Met His Gln Asp Trp Leu
                85                  90                  95

Asn Gly Lys Glu Phe Lys Cys Arg Val Asn Ser Ala Ala Phe Pro Ala
            100                 105                 110

Pro Ile Glu Lys Thr Ile Ser Lys Thr Lys Gly Arg Pro Lys Ala Pro
        115                 120                 125

Gln Val Tyr Thr Ile Pro Pro Pro Lys Glu Gln Met Ala Lys Asp Lys
    130                 135                 140

Val Ser Leu Thr Cys Met Ile Thr Asp Phe Phe Pro Glu Asp Ile Thr
145                 150                 155                 160

Val Glu Trp Gln Trp Asn Gly Gln Pro Ala Glu Asn Tyr Lys Asn Thr
                165                 170                 175

Gln Pro Ile Met Asp Thr Asp Gly Ser Tyr Phe Val Tyr Ser Lys Leu
            180                 185                 190

Asn Val Gln Lys Ser Asn Trp Glu Ala Gly Asn Thr Phe Thr Cys Ser
        195                 200                 205

Val Leu His Glu Gly Leu His Asn His His Thr Glu Lys Ser Leu Ser
    210                 215                 220

His Ser Pro Gly Ile His His His His His His His His
225                 230                 235
```

<210> SEQ ID NO 6
<211> LENGTH: 392
<212> TYPE: PRT
<213> ORGANISM: Artificial Sequence
<220> FEATURE:
<223> OTHER INFORMATION: Synthetic; 10H-MBPt

<400> SEQUENCE: 6

Met His His His His His His His His Gly Ser Lys Thr Glu
1               5                   10              15

Glu Gly Lys Leu Val Ile Trp Ile Asn Gly Asp Lys Gly Tyr Asn Gly
            20                  25                  30

Leu Ala Glu Val Gly Lys Lys Phe Glu Lys Asp Thr Gly Ile Lys Val
        35                  40                  45

Thr Val Glu His Pro Asp Lys Leu Glu Glu Lys Phe Pro Gln Val Ala
    50                  55                  60

Ala Thr Gly Asp Gly Pro Asp Ile Ile Phe Trp Ala His Asp Arg Phe
65                  70                  75                  80

Gly Gly Tyr Ala Gln Ser Gly Leu Leu Ala Glu Ile Thr Pro Asp Lys
            85                  90                  95

Ala Phe Gln Asp Lys Leu Tyr Pro Phe Thr Trp Asp Ala Val Arg Tyr
        100                 105                 110

Asn Gly Lys Leu Ile Ala Tyr Pro Ile Ala Val Glu Ala Leu Ser Leu
    115                 120                 125

Ile Tyr Asn Lys Asp Leu Leu Pro Asn Pro Pro Lys Thr Trp Glu Glu
    130                 135                 140

Ile Pro Ala Leu Asp Lys Glu Leu Lys Ala Lys Gly Lys Ser Ala Leu
145                 150                 155                 160

Met Phe Asn Leu Gln Glu Pro Tyr Phe Thr Trp Pro Leu Ile Ala Ala
            165                 170                 175

Asp Gly Gly Tyr Ala Phe Lys Tyr Glu Asn Gly Lys Tyr Asp Ile Lys
            180                 185                 190

Asp Val Gly Val Asp Asn Ala Gly Ala Lys Ala Gly Leu Thr Phe Leu
        195                 200                 205

Val Asp Leu Ile Lys Asn Lys His Met Asn Ala Asp Thr Asp Tyr Ser
    210                 215                 220

Ile Ala Glu Ala Ala Phe Asn Lys Gly Glu Thr Ala Met Thr Ile Asn
225                 230                 235                 240

Gly Pro Trp Ala Trp Ser Asn Ile Asp Thr Ser Lys Val Asn Tyr Gly
            245                 250                 255

Val Thr Val Leu Pro Thr Phe Lys Gly Gln Pro Ser Lys Pro Phe Val
        260                 265                 270

Gly Val Leu Ser Ala Gly Ile Asn Ala Ala Ser Pro Asn Lys Glu Leu
    275                 280                 285

Ala Lys Glu Phe Leu Glu Asn Tyr Leu Leu Thr Asp Glu Gly Leu Glu
290                 295                 300

Ala Val Asn Lys Asp Lys Pro Leu Gly Ala Val Ala Leu Lys Ser Tyr
305                 310                 315                 320

Glu Glu Glu Leu Ala Lys Asp Pro Arg Ile Ala Ala Thr Met Glu Asn
            325                 330                 335

Ala Gln Lys Gly Glu Ile Met Pro Asn Ile Pro Gln Met Ser Ala Phe
        340                 345                 350

Trp Tyr Ala Val Arg Thr Ala Val Ile Asn Ala Ala Ser Gly Arg Gln
    355                 360                 365

Thr Val Asp Glu Ala Leu Lys Asp Ala Gln Thr Asn Ser Ser Ser Gly
    370                 375                 380

Glu Asn Leu Tyr Phe Gln Gly Thr
385                 390

<210> SEQ ID NO 7
<211> LENGTH: 498

<212> TYPE: PRT
<213> ORGANISM: Artificial Sequence
<220> FEATURE:
<223> OTHER INFORMATION: Synthetic; recombinant CD38ecd-Fc-10H

<400> SEQUENCE: 7

```
Val Asp Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile Pro Pro Gly Val Pro Arg Asp Cys Gly Cys Lys Pro Cys Ile
            260                 265                 270

Cys Thr Val Pro Glu Val Ser Ser Val Phe Ile Phe Pro Pro Lys Pro
        275                 280                 285

Lys Asp Val Leu Thr Ile Thr Leu Thr Pro Lys Val Thr Cys Val Val
    290                 295                 300

Val Asp Ile Ser Lys Asp Asp Pro Glu Val Gln Phe Ser Trp Phe Val
305                 310                 315                 320

Asp Asp Val Glu Val His Thr Ala Gln Thr Gln Pro Arg Glu Glu Gln
                325                 330                 335

Phe Asn Ser Thr Phe Arg Ser Val Ser Glu Leu Pro Ile Met His Gln
            340                 345                 350

Asp Trp Leu Asn Gly Lys Glu Phe Lys Cys Arg Val Asn Ser Ala Ala
        355                 360                 365

Phe Pro Ala Pro Ile Glu Lys Thr Ile Ser Lys Thr Lys Gly Arg Pro
    370                 375                 380
```

-continued

```
Lys Ala Pro Gln Val Tyr Thr Ile Pro Pro Lys Glu Gln Met Ala
385                 390                 395                 400

Lys Asp Lys Val Ser Leu Thr Cys Met Ile Thr Asp Phe Phe Pro Glu
                405                 410                 415

Asp Ile Thr Val Glu Trp Gln Trp Asn Gly Gln Pro Ala Glu Asn Tyr
                420                 425                 430

Lys Asn Thr Gln Pro Ile Met Asp Thr Asp Gly Ser Tyr Phe Val Tyr
            435                 440                 445

Ser Lys Leu Asn Val Gln Lys Ser Asn Trp Glu Ala Gly Asn Thr Phe
450                 455                 460

Thr Cys Ser Val Leu His Glu Gly Leu His Asn His His Thr Glu Lys
465                 470                 475                 480

Ser Leu Ser His Ser Pro Gly Ile His His His His His His His
                485                 490                 495

His His
```

<210> SEQ ID NO 8
<211> LENGTH: 270
<212> TYPE: PRT
<213> ORGANISM: Artificial Sequence
<220> FEATURE:
<223> OTHER INFORMATION: Synthetic; recombinant CD38ecd-10H

<400> SEQUENCE: 8

```
Val Asp Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
                20                  25                  30

Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
        50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
                100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
```

```
                        245                 250                 255

Glu Ile Gly Ile His His His His His His His His
                260                 265                 270

<210> SEQ ID NO 9
<211> LENGTH: 648
<212> TYPE: PRT
<213> ORGANISM: Artificial Sequence
<220> FEATURE:
<223> OTHER INFORMATION: Synthetic; recombinant 10H-MBPt-CD38ecd

<400> SEQUENCE: 9

Met His His His His His His His His His Gly Ser Lys Thr Glu
1               5                   10                  15

Glu Gly Lys Leu Val Ile Trp Ile Asn Gly Asp Lys Gly Tyr Asn Gly
            20                  25                  30

Leu Ala Glu Val Gly Lys Lys Phe Glu Lys Asp Thr Gly Ile Lys Val
        35                  40                  45

Thr Val Glu His Pro Asp Lys Leu Glu Glu Lys Phe Pro Gln Val Ala
    50                  55                  60

Ala Thr Gly Asp Gly Pro Asp Ile Ile Phe Trp Ala His Asp Arg Phe
65                  70                  75                  80

Gly Gly Tyr Ala Gln Ser Gly Leu Leu Ala Glu Ile Thr Pro Asp Lys
                85                  90                  95

Ala Phe Gln Asp Lys Leu Tyr Pro Phe Thr Trp Asp Ala Val Arg Tyr
            100                 105                 110

Asn Gly Lys Leu Ile Ala Tyr Pro Ile Ala Val Glu Ala Leu Ser Leu
        115                 120                 125

Ile Tyr Asn Lys Asp Leu Leu Pro Asn Pro Pro Lys Thr Trp Glu Glu
    130                 135                 140

Ile Pro Ala Leu Asp Lys Glu Leu Lys Ala Lys Gly Lys Ser Ala Leu
145                 150                 155                 160

Met Phe Asn Leu Gln Glu Pro Tyr Phe Thr Trp Pro Leu Ile Ala Ala
                165                 170                 175

Asp Gly Gly Tyr Ala Phe Lys Tyr Glu Asn Gly Lys Tyr Asp Ile Lys
            180                 185                 190

Asp Val Gly Val Asp Asn Ala Gly Ala Lys Ala Gly Leu Thr Phe Leu
        195                 200                 205

Val Asp Leu Ile Lys Asn Lys His Met Asn Ala Asp Thr Asp Tyr Ser
    210                 215                 220

Ile Ala Glu Ala Ala Phe Asn Lys Gly Glu Thr Ala Met Thr Ile Asn
225                 230                 235                 240

Gly Pro Trp Ala Trp Ser Asn Ile Asp Thr Ser Lys Val Asn Tyr Gly
                245                 250                 255

Val Thr Val Leu Pro Thr Phe Lys Gly Gln Pro Ser Lys Pro Phe Val
            260                 265                 270

Gly Val Leu Ser Ala Gly Ile Asn Ala Ala Ser Pro Asn Lys Glu Leu
        275                 280                 285

Ala Lys Glu Phe Leu Glu Asn Tyr Leu Leu Thr Asp Glu Gly Leu Glu
    290                 295                 300

Ala Val Asn Lys Asp Lys Pro Leu Gly Ala Val Ala Leu Lys Ser Tyr
305                 310                 315                 320

Glu Glu Glu Leu Ala Lys Asp Pro Arg Ile Ala Ala Thr Met Glu Asn
                325                 330                 335

Ala Gln Lys Gly Glu Ile Met Pro Asn Ile Pro Gln Met Ser Ala Phe
```

```
            340                 345                 350
Trp Tyr Ala Val Arg Thr Ala Val Ile Asn Ala Ala Ser Gly Arg Gln
            355                 360                 365
Thr Val Asp Glu Ala Leu Lys Asp Ala Gln Thr Asn Ser Ser Ser Gly
        370                 375                 380
Glu Asn Leu Tyr Phe Gln Gly Thr Arg Trp Arg Gln Gln Trp Ser Gly
385                 390                 395                 400
Pro Gly Thr Thr Lys Arg Phe Pro Glu Thr Val Leu Ala Arg Cys Val
            405                 410                 415
Lys Tyr Thr Glu Ile His Pro Glu Met Arg His Val Asp Cys Gln Ser
        420                 425                 430
Val Trp Asp Ala Phe Lys Gly Ala Phe Ile Ser Lys His Pro Cys Asn
            435                 440                 445
Ile Thr Glu Glu Asp Tyr Gln Pro Leu Met Lys Leu Gly Thr Gln Thr
        450                 455                 460
Val Pro Cys Asn Lys Ile Leu Leu Trp Ser Arg Ile Lys Asp Leu Ala
465                 470                 475                 480
His Gln Phe Thr Gln Val Gln Arg Asp Met Phe Thr Leu Glu Asp Thr
            485                 490                 495
Leu Leu Gly Tyr Leu Ala Asp Asp Leu Thr Trp Cys Gly Glu Phe Asn
            500                 505                 510
Thr Ser Lys Ile Asn Tyr Gln Ser Cys Pro Asp Trp Arg Lys Asp Cys
        515                 520                 525
Ser Asn Asn Pro Val Ser Val Phe Trp Lys Thr Val Ser Arg Arg Phe
    530                 535                 540
Ala Glu Ala Ala Cys Asp Val Val His Val Met Leu Asn Gly Ser Arg
545                 550                 555                 560
Ser Lys Ile Phe Asp Lys Asn Ser Thr Phe Gly Ser Val Glu Val His
            565                 570                 575
Asn Leu Gln Pro Glu Lys Val Gln Thr Leu Glu Ala Trp Val Ile His
            580                 585                 590
Gly Gly Arg Glu Asp Ser Arg Asp Leu Cys Gln Asp Pro Thr Ile Lys
        595                 600                 605
Glu Leu Glu Ser Ile Ile Ser Lys Arg Asn Ile Gln Phe Ser Cys Lys
        610                 615                 620
Asn Ile Tyr Arg Pro Asp Lys Phe Leu Gln Cys Val Lys Asn Pro Glu
625                 630                 635                 640
Asp Ser Ser Cys Thr Ser Glu Ile
            645

<210> SEQ ID NO 10
<211> LENGTH: 278
<212> TYPE: PRT
<213> ORGANISM: Artificial Sequence
<220> FEATURE:
<223> OTHER INFORMATION: Synthetic; recombinant 10Ht-CD38ecd

<400> SEQUENCE: 10

Met His His His His His His His His His Gly Ser Gly Glu Asn
1               5                   10                  15
Leu Tyr Phe Gln Gly Thr Arg Trp Arg Gln Gln Trp Ser Gly Pro Gly
            20                  25                  30
Thr Thr Lys Arg Phe Pro Glu Thr Val Leu Ala Arg Cys Val Lys Tyr
        35                  40                  45
Thr Glu Ile His Pro Glu Met Arg His Val Asp Cys Gln Ser Val Trp
```

```
                    50                  55                  60
Asp Ala Phe Lys Gly Ala Phe Ile Ser Lys His Pro Cys Asn Ile Thr
 65                  70                  75                  80

Glu Glu Asp Tyr Gln Pro Leu Met Lys Leu Gly Thr Gln Thr Val Pro
                     85                  90                  95

Cys Asn Lys Ile Leu Leu Trp Ser Arg Ile Lys Asp Leu Ala His Gln
                100                 105                 110

Phe Thr Gln Val Gln Arg Asp Met Phe Thr Leu Glu Asp Thr Leu Leu
                115                 120                 125

Gly Tyr Leu Ala Asp Asp Leu Thr Trp Cys Gly Glu Phe Asn Thr Ser
            130                 135                 140

Lys Ile Asn Tyr Gln Ser Cys Pro Asp Trp Arg Lys Asp Cys Ser Asn
145                 150                 155                 160

Asn Pro Val Ser Val Phe Trp Lys Thr Val Ser Arg Arg Phe Ala Glu
                165                 170                 175

Ala Ala Cys Asp Val Val His Val Met Leu Asn Gly Ser Arg Ser Lys
                180                 185                 190

Ile Phe Asp Lys Asn Ser Thr Phe Gly Ser Val Glu Val His Asn Leu
                195                 200                 205

Gln Pro Glu Lys Val Gln Thr Leu Glu Ala Trp Val Ile His Gly Gly
    210                 215                 220

Arg Glu Asp Ser Arg Asp Leu Cys Gln Asp Pro Thr Ile Lys Glu Leu
225                 230                 235                 240

Glu Ser Ile Ile Ser Lys Arg Asn Ile Gln Phe Ser Cys Lys Asn Ile
                245                 250                 255

Tyr Arg Pro Asp Lys Phe Leu Gln Cys Val Lys Asn Pro Glu Asp Ser
                260                 265                 270

Ser Cys Thr Ser Glu Ile
            275

<210> SEQ ID NO 11
<211> LENGTH: 443
<212> TYPE: PRT
<213> ORGANISM: Artificial Sequence
<220> FEATURE:
<223> OTHER INFORMATION: Synthetic; recombinant 10H-MBPt-DARAepitopes

<400> SEQUENCE: 11

Met His His His His His His His His Gly Ser Lys Thr Glu
 1               5                  10                  15

Glu Gly Lys Leu Val Ile Trp Ile Asn Gly Asp Lys Gly Tyr Asn Gly
                 20                  25                  30

Leu Ala Glu Val Gly Lys Lys Phe Glu Lys Asp Thr Gly Ile Lys Val
             35                  40                  45

Thr Val Glu His Pro Asp Lys Leu Glu Glu Lys Phe Pro Gln Val Ala
 50                  55                  60

Ala Thr Gly Asp Gly Pro Asp Ile Ile Phe Trp Ala His Asp Arg Phe
 65                  70                  75                  80

Gly Gly Tyr Ala Gln Ser Gly Leu Leu Ala Glu Ile Thr Pro Asp Lys
                 85                  90                  95

Ala Phe Gln Asp Lys Leu Tyr Pro Phe Thr Trp Asp Ala Val Arg Tyr
                100                 105                 110

Asn Gly Lys Leu Ile Ala Tyr Pro Ile Ala Val Glu Ala Leu Ser Leu
            115                 120                 125

Ile Tyr Asn Lys Asp Leu Leu Pro Asn Pro Pro Lys Thr Trp Glu Glu
```

```
                130             135             140
Ile Pro Ala Leu Asp Lys Glu Leu Lys Ala Lys Gly Lys Ser Ala Leu
145                 150                 155                 160

Met Phe Asn Leu Gln Glu Pro Tyr Phe Thr Trp Pro Leu Ile Ala Ala
                165                 170                 175

Asp Gly Gly Tyr Ala Phe Lys Tyr Glu Asn Gly Lys Tyr Asp Ile Lys
            180                 185                 190

Asp Val Gly Val Asp Asn Ala Gly Ala Lys Ala Gly Leu Thr Phe Leu
                195                 200                 205

Val Asp Leu Ile Lys Asn Lys His Met Asn Ala Asp Thr Asp Tyr Ser
    210                 215                 220

Ile Ala Glu Ala Ala Phe Asn Lys Gly Glu Thr Ala Met Thr Ile Asn
225                 230                 235                 240

Gly Pro Trp Ala Trp Ser Asn Ile Asp Thr Ser Lys Val Asn Tyr Gly
                245                 250                 255

Val Thr Val Leu Pro Thr Phe Lys Gly Gln Pro Ser Lys Pro Phe Val
                260                 265                 270

Gly Val Leu Ser Ala Gly Ile Asn Ala Ala Ser Pro Asn Lys Glu Leu
            275                 280                 285

Ala Lys Glu Phe Leu Glu Asn Tyr Leu Leu Thr Asp Glu Gly Leu Glu
    290                 295                 300

Ala Val Asn Lys Asp Lys Pro Leu Gly Ala Val Ala Leu Lys Ser Tyr
305                 310                 315                 320

Glu Glu Glu Leu Ala Lys Asp Pro Arg Ile Ala Ala Thr Met Glu Asn
                325                 330                 335

Ala Gln Lys Gly Glu Ile Met Pro Asn Ile Pro Gln Met Ser Ala Phe
            340                 345                 350

Trp Tyr Ala Val Arg Thr Ala Val Ile Asn Ala Ala Ser Gly Arg Gln
                355                 360                 365

Thr Val Asp Glu Ala Leu Lys Asp Ala Gln Thr Asn Ser Ser Ser Gly
                370                 375                 380

Glu Asn Leu Tyr Phe Gln Gly Thr Leu Gln Pro Glu Lys Val Gln Thr
385                 390                 395                 400

Leu Glu Ala Trp Val Ile His Gly Gly Arg Glu Asp Ser Arg Asp Leu
                405                 410                 415

Cys Gln Asp Pro Thr Ile Lys Glu Leu Glu Ser Ile Ile Ser Lys Arg
                420                 425                 430

Asn Ile Gln Phe Ser Cys Lys Asn Ile Tyr Arg
            435                 440

<210> SEQ ID NO 12
<211> LENGTH: 497
<212> TYPE: PRT
<213> ORGANISM: Artificial Sequence
<220> FEATURE:
<223> OTHER INFORMATION: Synthetic; recombinant extracellular domain of
      CD38

<400> SEQUENCE: 12

Val Asp Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
                20                  25                  30

Pro Glu Met Arg His Val Asp Cys Gln Ser Val Trp Asp Ala Phe Lys
            35                  40                  45
```

-continued

Gly Ala Phe Ile Ser Lys His Pro Cys Asn Ile Thr Glu Glu Asp Tyr
        50                  55                  60

Gln Pro Leu Met Lys Leu Gly Thr Gln Thr Val Pro Cys Asn Lys Ile
 65                  70                  75                  80

Leu Leu Trp Ser Arg Ile Lys Asp Leu Ala His Gln Phe Thr Gln Val
                 85                  90                  95

Gln Arg Asp Met Phe Thr Leu Glu Asp Thr Leu Leu Gly Tyr Leu Ala
                100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile Pro Pro Gly Gly Gly Ser Gly Gly Gly Ser Gly Gly Gly Gly
            260                 265                 270

Ser Val Pro Glu Val Ser Val Phe Ile Phe Pro Pro Lys Pro Lys
        275                 280                 285

Asp Val Leu Thr Ile Thr Leu Thr Pro Lys Val Thr Cys Val Val Val
    290                 295                 300

Asp Ile Ser Lys Asp Asp Pro Glu Val Gln Phe Ser Trp Phe Val Asp
305                 310                 315                 320

Asp Val Glu Val His Thr Ala Gln Thr Gln Pro Arg Glu Glu Gln Phe
                325                 330                 335

Asn Ser Thr Phe Arg Ser Val Ser Glu Leu Pro Ile Met His Gln Asp
            340                 345                 350

Trp Leu Asn Gly Lys Glu Phe Lys Cys Arg Val Asn Ser Ala Ala Phe
        355                 360                 365

Pro Ala Pro Ile Glu Lys Thr Ile Ser Lys Thr Lys Gly Arg Pro Lys
    370                 375                 380

Ala Pro Gln Val Tyr Thr Ile Pro Pro Pro Lys Glu Gln Met Ala Lys
385                 390                 395                 400

Asp Lys Val Ser Leu Thr Cys Met Ile Thr Asp Phe Phe Pro Glu Asp
                405                 410                 415

Ile Thr Val Glu Trp Gln Trp Asn Gly Gln Pro Ala Glu Asn Tyr Lys
            420                 425                 430

Asn Thr Gln Pro Ile Met Asp Thr Asp Gly Ser Tyr Phe Val Tyr Ser
        435                 440                 445

Lys Leu Asn Val Gln Lys Ser Asn Trp Glu Ala Gly Asn Thr Phe Thr
    450                 455                 460

Cys Ser Val Leu His Glu Gly Leu His Asn His His Thr Glu Lys Ser

```
              465                 470                 475                 480

Leu Ser His Ser Pro Gly Ile His His His His His His His
                    485                 490                 495

His

<210> SEQ ID NO 13
<211> LENGTH: 488
<212> TYPE: PRT
<213> ORGANISM: Artificial Sequence
<220> FEATURE:
<223> OTHER INFORMATION: Synthetic; recombinant extracellular domain of
      CD38

<400> SEQUENCE: 13

Val Asp Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
                20                  25                  30

Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile Pro Pro Gly Val Pro Arg Asp Cys Gly Cys Lys Pro Cys Ile
            260                 265                 270

Cys Thr Val Pro Glu Val Ser Ser Val Phe Ile Phe Pro Pro Lys Pro
            275                 280                 285

Lys Asp Val Leu Thr Ile Thr Leu Thr Pro Lys Val Thr Cys Val Val
290                 295                 300

Val Asp Ile Ser Lys Asp Asp Pro Glu Val Gln Phe Ser Trp Phe Val
305                 310                 315                 320

Asp Asp Val Glu Val His Thr Ala Gln Thr Gln Pro Arg Glu Glu Gln
```

```
                        325                 330                 335
Phe Asn Ser Thr Phe Arg Ser Val Ser Glu Leu Pro Ile Met His Gln
                    340                 345                 350

Asp Trp Leu Asn Gly Lys Glu Phe Lys Cys Arg Val Asn Ser Ala Ala
                355                 360                 365

Phe Pro Ala Pro Ile Glu Lys Thr Ile Ser Lys Thr Lys Gly Arg Pro
            370                 375                 380

Lys Ala Pro Gln Val Tyr Thr Ile Pro Pro Lys Glu Gln Met Ala
385                 390                 395                 400

Lys Asp Lys Val Ser Leu Thr Cys Met Ile Thr Asp Phe Phe Pro Glu
                405                 410                 415

Asp Ile Thr Val Glu Trp Gln Trp Asn Gly Gln Pro Ala Glu Asn Tyr
                420                 425                 430

Lys Asn Thr Gln Pro Ile Met Asp Thr Asp Gly Ser Tyr Phe Val Tyr
                435                 440                 445

Ser Lys Leu Asn Val Gln Lys Ser Asn Trp Glu Ala Gly Asn Thr Phe
450                 455                 460

Thr Cys Ser Val Leu His Glu Gly Leu His Asn His His Thr Glu Lys
465                 470                 475                 480

Ser Leu Ser His Ser Pro Gly Ile
                485

<210> SEQ ID NO 14
<211> LENGTH: 281
<212> TYPE: PRT
<213> ORGANISM: Artificial Sequence
<220> FEATURE:
<223> OTHER INFORMATION: Synthetic; recombinant extracellular domain of
      CD38

<400> SEQUENCE: 14

Val Asp Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
                20                  25                  30

Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
        50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
                100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
                180                 185                 190
```

```
Val Gln Thr Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile Pro Pro Gly Gly Gly Gly Ser Gly Gly Gly Ser His
            260                 265                 270

His His His His His His His His
        275                 280

<210> SEQ ID NO 15
<211> LENGTH: 252
<212> TYPE: PRT
<213> ORGANISM: Artificial Sequence
<220> FEATURE:
<223> OTHER INFORMATION: Synthetic; immunoglobulin Fc region

<400> SEQUENCE: 15

Val Asp Arg Ser Arg Ile Arg Thr Ile Ser Ala Arg Leu Glu Tyr Thr
1               5                   10                  15

Arg Pro His Arg Ser Asp Leu Pro Gly Val Pro Arg Asp Cys Gly Cys
            20                  25                  30

Lys Pro Cys Ile Cys Thr Val Pro Glu Val Ser Ser Val Phe Ile Phe
        35                  40                  45

Pro Pro Lys Pro Lys Asp Val Leu Thr Ile Thr Leu Thr Pro Lys Val
50                  55                  60

Thr Cys Val Val Val Asp Ile Ser Lys Asp Asp Pro Glu Val Gln Phe
65                  70                  75                  80

Ser Trp Phe Val Asp Asp Val Glu Val His Thr Ala Gln Thr Gln Pro
                85                  90                  95

Arg Glu Glu Gln Phe Asn Ser Thr Phe Arg Ser Val Ser Glu Leu Pro
            100                 105                 110

Ile Met His Gln Asp Trp Leu Asn Gly Lys Glu Phe Lys Cys Arg Val
        115                 120                 125

Asn Ser Ala Ala Phe Pro Ala Pro Ile Glu Lys Thr Ile Ser Lys Thr
130                 135                 140

Lys Gly Arg Pro Lys Ala Pro Gln Val Tyr Thr Ile Pro Pro Pro Lys
145                 150                 155                 160

Glu Gln Met Ala Lys Asp Lys Val Ser Leu Thr Cys Met Ile Thr Asp
                165                 170                 175

Phe Phe Pro Glu Asp Ile Thr Val Glu Trp Gln Trp Asn Gly Gln Pro
            180                 185                 190

Ala Glu Asn Tyr Lys Asn Thr Gln Pro Ile Met Asp Thr Asp Gly Ser
        195                 200                 205

Tyr Phe Val Tyr Ser Lys Leu Asn Val Gln Lys Ser Asn Trp Glu Ala
210                 215                 220

Gly Asn Thr Phe Thr Cys Ser Val Leu His Glu Gly Leu His Asn His
225                 230                 235                 240

His Thr Glu Lys Ser Leu Ser His Ser Pro Gly Ile
                245                 250

<210> SEQ ID NO 16
<211> LENGTH: 262
```

```
<212> TYPE: PRT
<213> ORGANISM: Artificial Sequence
<220> FEATURE:
<223> OTHER INFORMATION: Synthetic; recombinant polypeptide

<400> SEQUENCE: 16

Val Asp Arg Ser Arg Ile Arg Thr Ile Ser Ala Arg Leu Glu Tyr Thr
1               5                   10                  15

Arg Pro His Arg Ser Asp Leu Pro Gly Val Pro Arg Asp Cys Gly Cys
            20                  25                  30

Lys Pro Cys Ile Cys Thr Val Pro Glu Val Ser Ser Val Phe Ile Phe
        35                  40                  45

Pro Pro Lys Pro Lys Asp Val Leu Thr Ile Thr Leu Thr Pro Lys Val
50                  55                  60

Thr Cys Val Val Val Asp Ile Ser Lys Asp Asp Pro Glu Val Gln Phe
65                  70                  75                  80

Ser Trp Phe Val Asp Asp Val Glu Val His Thr Ala Gln Thr Gln Pro
                85                  90                  95

Arg Glu Glu Gln Phe Asn Ser Thr Phe Arg Ser Val Ser Glu Leu Pro
            100                 105                 110

Ile Met His Gln Asp Trp Leu Asn Gly Lys Glu Phe Lys Cys Arg Val
        115                 120                 125

Asn Ser Ala Ala Phe Pro Ala Pro Ile Glu Lys Thr Ile Ser Lys Thr
130                 135                 140

Lys Gly Arg Pro Lys Ala Pro Gln Val Tyr Thr Ile Pro Pro Pro Lys
145                 150                 155                 160

Glu Gln Met Ala Lys Asp Lys Val Ser Leu Thr Cys Met Ile Thr Asp
                165                 170                 175

Phe Phe Pro Glu Asp Ile Thr Val Glu Trp Gln Trp Asn Gly Gln Pro
            180                 185                 190

Ala Glu Asn Tyr Lys Asn Thr Gln Pro Ile Met Asp Thr Asp Gly Ser
        195                 200                 205

Tyr Phe Val Tyr Ser Lys Leu Asn Val Gln Lys Ser Asn Trp Glu Ala
210                 215                 220

Gly Asn Thr Phe Thr Cys Ser Val Leu His Glu Gly Leu His Asn His
225                 230                 235                 240

His Thr Glu Lys Ser Leu Ser His Ser Pro Gly Ile His His His
                245                 250                 255

His His His His His His
            260

<210> SEQ ID NO 17
<211> LENGTH: 261
<212> TYPE: PRT
<213> ORGANISM: Artificial Sequence
<220> FEATURE:
<223> OTHER INFORMATION: Synthetic; recombinant polypeptide

<400> SEQUENCE: 17

Val Asp Arg Ser Arg Ile Arg Thr Ile Ser Ala Arg Leu Glu Tyr Thr
1               5                   10                  15

Arg Pro His Arg Ser Asp Leu Pro Gly Gly Gly Ser Gly Gly Gly
            20                  25                  30

Ser Gly Gly Gly Ser Val Pro Glu Val Ser Ser Val Phe Ile Phe Pro
        35                  40                  45

Pro Lys Pro Lys Asp Val Leu Thr Ile Thr Leu Thr Pro Lys Val Thr
50                  55                  60
```

Cys Val Val Asp Ile Ser Lys Asp Asp Pro Glu Val Gln Phe Ser
65                  70                  75                  80

Trp Phe Val Asp Val Glu Val His Thr Ala Gln Thr Gln Pro Arg
                85                  90                  95

Glu Glu Gln Phe Asn Ser Thr Phe Arg Ser Val Ser Glu Leu Pro Ile
            100                 105                 110

Met His Gln Asp Trp Leu Asn Gly Lys Glu Phe Lys Cys Arg Val Asn
            115                 120                 125

Ser Ala Ala Phe Pro Ala Pro Ile Glu Lys Thr Ile Ser Lys Thr Lys
130                 135                 140

Gly Arg Pro Lys Ala Pro Gln Val Tyr Thr Ile Pro Pro Lys Glu
145                 150                 155                 160

Gln Met Ala Lys Asp Lys Val Ser Leu Thr Cys Met Ile Thr Asp Phe
                165                 170                 175

Phe Pro Glu Asp Ile Thr Val Glu Trp Gln Trp Asn Gly Gln Pro Ala
            180                 185                 190

Glu Asn Tyr Lys Asn Thr Gln Pro Ile Met Asp Thr Asp Gly Ser Tyr
            195                 200                 205

Phe Val Tyr Ser Lys Leu Asn Val Gln Lys Ser Asn Trp Glu Ala Gly
210                 215                 220

Asn Thr Phe Thr Cys Ser Val Leu His Glu Gly Leu His Asn His His
225                 230                 235                 240

Thr Glu Lys Ser Leu Ser His Ser Pro Gly Ile His His His His
                245                 250                 255

His His His His His
            260

<210> SEQ ID NO 18
<211> LENGTH: 236
<212> TYPE: PRT
<213> ORGANISM: Artificial Sequence
<220> FEATURE:
<223> OTHER INFORMATION: Synthetic; recombinant polypeptide

<400> SEQUENCE: 18

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
            35                  40                  45

Asp Asp Pro Glu Val Gln Phe Ser Trp Phe Val Asp Asp Val Glu Val
50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
            115                 120                 125

Tyr Thr Ile Pro Pro Pro Lys Glu Gln Met Ala Lys Asp Lys Val Ser
130                 135                 140

Leu Thr Cys Met Ile Thr Asp Phe Phe Pro Glu Asp Ile Thr Val Glu
145                 150                 155                 160

```
Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Ile Gly His His His His His His
225                 230                 235
```

<210> SEQ ID NO 19
<211> LENGTH: 421
<212> TYPE: PRT
<213> ORGANISM: Artificial Sequence
<220> FEATURE:
<223> OTHER INFORMATION: Synthetic; recombinant polypeptide

<400> SEQUENCE: 19

```
Met His His His His His His His His His Gly Ser Lys Thr Glu
1               5                   10                  15

Glu Gly Lys Leu Val Ile Trp Ile Asn Gly Asp Lys Gly Tyr Asn Gly
                20                  25                  30

Leu Ala Glu Val Gly Lys Lys Phe Glu Lys Asp Thr Gly Ile Lys Val
            35                  40                  45

Thr Val Glu His Pro Asp Lys Leu Glu Glu Lys Phe Pro Gln Val Ala
        50                  55                  60

Ala Thr Gly Asp Gly Pro Asp Ile Ile Phe Trp Ala His Asp Arg Phe
65                  70                  75                  80

Gly Gly Tyr Ala Gln Ser Gly Leu Leu Ala Glu Ile Thr Pro Asp Lys
                85                  90                  95

Ala Phe Gln Asp Lys Leu Tyr Pro Phe Thr Trp Asp Ala Val Arg Tyr
            100                 105                 110

Asn Gly Lys Leu Ile Ala Tyr Pro Ile Ala Val Glu Ala Leu Ser Leu
        115                 120                 125

Ile Tyr Asn Lys Asp Leu Leu Pro Asn Pro Pro Lys Thr Trp Glu Glu
130                 135                 140

Ile Pro Ala Leu Asp Lys Glu Leu Lys Ala Lys Gly Lys Ser Ala Leu
145                 150                 155                 160

Met Phe Asn Leu Gln Glu Pro Tyr Phe Thr Trp Pro Leu Ile Ala Ala
                165                 170                 175

Asp Gly Gly Tyr Ala Phe Lys Tyr Glu Asn Gly Lys Tyr Asp Ile Lys
            180                 185                 190

Asp Val Gly Val Asp Asn Ala Gly Ala Lys Ala Gly Leu Thr Phe Leu
        195                 200                 205

Val Asp Leu Ile Lys Asn Lys His Met Asn Ala Asp Thr Asp Tyr Ser
210                 215                 220

Ile Ala Glu Ala Ala Phe Asn Lys Gly Glu Thr Ala Met Thr Ile Asn
225                 230                 235                 240

Gly Pro Trp Ala Trp Ser Asn Ile Asp Thr Ser Lys Val Asn Tyr Gly
                245                 250                 255

Val Thr Val Leu Pro Thr Phe Lys Gly Gln Pro Ser Lys Pro Phe Val
            260                 265                 270

Gly Val Leu Ser Ala Gly Ile Asn Ala Ala Ser Pro Asn Lys Glu Leu
        275                 280                 285
```

```
Ala Lys Glu Phe Leu Glu Asn Tyr Leu Leu Thr Asp Glu Gly Leu Glu
        290                 295                 300

Ala Val Asn Lys Asp Lys Pro Leu Gly Ala Val Ala Leu Lys Ser Tyr
305                 310                 315                 320

Glu Glu Glu Leu Ala Lys Asp Pro Arg Ile Ala Ala Thr Met Glu Asn
                325                 330                 335

Ala Gln Lys Gly Glu Ile Met Pro Asn Ile Pro Gln Met Ser Ala Phe
            340                 345                 350

Trp Tyr Ala Val Arg Thr Ala Val Ile Asn Ala Ala Ser Gly Arg Gln
        355                 360                 365

Thr Val Asp Glu Ala Leu Lys Asp Ala Gln Thr Asn Ser Ser Ser Gly
    370                 375                 380

Glu Asn Leu Tyr Phe Gln Gly Thr Gly Thr Ser Asn Ala Ser Arg Ser
385                 390                 395                 400

Ala Gly Ser Thr Pro Gly Ser Ser Gly Arg Thr Ser Pro Ser Pro Ser
                405                 410                 415

Leu Ser Leu Ile Ser
            420

<210> SEQ ID NO 20
<211> LENGTH: 365
<212> TYPE: PRT
<213> ORGANISM: Artificial Sequence
<220> FEATURE:
<223> OTHER INFORMATION: Synthetic; recombinant polypeptide

<400> SEQUENCE: 20

Val Asp Gln Leu Leu Phe Asn Lys Thr Lys Ser Val Glu Phe Thr Phe
1               5                   10                  15

Cys Asn Asp Thr Val Val Ile Pro Cys Phe Val Thr Asn Met Glu Ala
                20                  25                  30

Gln Asn Thr Thr Glu Val Tyr Val Lys Trp Lys Phe Lys Gly Arg Asp
            35                  40                  45

Ile Tyr Thr Phe Asp Gly Ala Leu Asn Lys Ser Thr Val Pro Thr Asp
        50                  55                  60

Phe Ser Ser Ala Lys Ile Glu Val Ser Gln Leu Leu Lys Gly Asp Ala
65                  70                  75                  80

Ser Leu Lys Met Asp Lys Ser Asp Ala Val Ser His Thr Gly Asn Tyr
                85                  90                  95

Thr Cys Glu Val Thr Glu Leu Thr Arg Glu Gly Glu Thr Ile Ile Glu
            100                 105                 110

Leu Lys Tyr Arg Val Val Ser Trp Phe Ser Pro Asn Glu Gly Pro Gly
        115                 120                 125

Val Pro Arg Asp Cys Gly Cys Lys Pro Cys Ile Cys Thr Val Pro Glu
    130                 135                 140

Val Ser Ser Val Phe Ile Phe Pro Pro Lys Pro Lys Asp Val Leu Thr
145                 150                 155                 160

Ile Thr Leu Thr Pro Lys Val Thr Cys Val Val Val Asp Ile Ser Lys
                165                 170                 175

Asp Asp Pro Glu Val Gln Phe Ser Trp Phe Val Asp Asp Val Glu Val
            180                 185                 190

His Thr Ala Gln Thr Gln Pro Arg Glu Glu Gln Phe Asn Ser Thr Phe
        195                 200                 205

Arg Ser Val Ser Glu Leu Pro Ile Met His Gln Asp Trp Leu Asn Gly
    210                 215                 220
```

```
Lys Glu Phe Lys Cys Arg Val Asn Ser Ala Ala Phe Pro Ala Pro Ile
225                 230                 235                 240

Glu Lys Thr Ile Ser Lys Thr Lys Gly Arg Pro Lys Ala Pro Gln Val
            245                 250                 255

Tyr Thr Ile Pro Pro Lys Glu Gln Met Ala Lys Asp Lys Val Ser
        260                 265                 270

Leu Thr Cys Met Ile Thr Asp Phe Phe Pro Glu Asp Ile Thr Val Glu
        275                 280                 285

Trp Gln Trp Asn Gly Gln Pro Ala Glu Asn Tyr Lys Asn Thr Gln Pro
            290                 295                 300

Ile Met Asp Thr Asp Gly Ser Tyr Phe Val Tyr Ser Lys Leu Asn Val
305                 310                 315                 320

Gln Lys Ser Asn Trp Glu Ala Gly Asn Thr Phe Thr Cys Ser Val Leu
                325                 330                 335

His Glu Gly Leu His Asn His His Thr Glu Lys Ser Leu Ser His Ser
                340                 345                 350

Pro Gly Ile His His His His His His His His
            355                 360                 365
```

```
<210> SEQ ID NO 21
<211> LENGTH: 526
<212> TYPE: PRT
<213> ORGANISM: Artificial Sequence
<220> FEATURE:
<223> OTHER INFORMATION: Synthetic; recombinant polypeptide

<400> SEQUENCE: 21

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220
```

-continued

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
            245                 250                 255

Tyr Lys Tyr Pro Gly Lys Gly Cys Pro Thr Leu Gly Asp Glu Gly Asp
        260                 265                 270

Thr Asp Leu Tyr Asp Tyr Tyr Pro Glu Glu Asp Thr Glu Gly Asp Lys
    275                 280                 285

Val Arg Val Pro Arg Asp Cys Gly Cys Lys Pro Cys Ile Cys Thr Val
290                 295                 300

Pro Glu Val Ser Ser Val Phe Ile Phe Pro Lys Pro Lys Asp Val
305                 310                 315                 320

Leu Thr Ile Thr Leu Thr Pro Lys Val Thr Cys Val Val Asp Ile
            325                 330                 335

Ser Lys Asp Asp Pro Glu Val Gln Phe Ser Trp Phe Val Asp Val
            340                 345                 350

Glu Val His Thr Ala Gln Thr Gln Pro Arg Glu Glu Gln Phe Asn Ser
        355                 360                 365

Thr Phe Arg Ser Val Ser Glu Leu Pro Ile Met His Gln Asp Trp Leu
    370                 375                 380

Asn Gly Lys Glu Phe Lys Cys Arg Val Asn Ser Ala Ala Phe Pro Ala
385                 390                 395                 400

Pro Ile Glu Lys Thr Ile Ser Lys Thr Lys Gly Arg Pro Lys Ala Pro
            405                 410                 415

Gln Val Tyr Thr Ile Pro Pro Lys Glu Gln Met Ala Lys Asp Lys
        420                 425                 430

Val Ser Leu Thr Cys Met Ile Thr Asp Phe Phe Pro Glu Asp Ile Thr
        435                 440                 445

Val Glu Trp Gln Trp Asn Gly Gln Pro Ala Glu Asn Tyr Lys Asn Thr
    450                 455                 460

Gln Pro Ile Met Asp Thr Asp Gly Ser Tyr Phe Val Tyr Ser Lys Leu
465                 470                 475                 480

Asn Val Gln Lys Ser Asn Trp Glu Ala Gly Asn Thr Phe Thr Cys Ser
            485                 490                 495

Val Leu His Glu Gly Leu His Asn His His Thr Glu Lys Ser Leu Ser
        500                 505                 510

His Ser Pro Gly Ile Gly His His His His His His
        515                 520                 525

<210> SEQ ID NO 22
<211> LENGTH: 334
<212> TYPE: PRT
<213> ORGANISM: Artificial Sequence
<220> FEATURE:
<223> OTHER INFORMATION: Synthetic; recombinant polypeptide

<400> SEQUENCE: 22

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

```
Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Met Asp Glu Lys Thr Thr Gly Trp Arg Gly His Val Val
    290                 295                 300

Glu Gly Leu Ala Gly Glu Leu Glu Gln Leu Arg Ala Arg Leu Glu His
305                 310                 315                 320

His Pro Gln Gly Gln Arg Glu Pro His His His His His
                325                 330

<210> SEQ ID NO 23
<211> LENGTH: 296
<212> TYPE: PRT
<213> ORGANISM: Artificial Sequence
<220> FEATURE:
<223> OTHER INFORMATION: Synthetic; recombinant polypeptide

<400> SEQUENCE: 23

His Pro Ile Cys Glu Val Ser Lys Val Ala Ser His Leu Glu Val Asn
 1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
 50                  55                  60

Ser Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95
```

```
Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg His His His His His
    290                 295

<210> SEQ ID NO 24
<211> LENGTH: 336
<212> TYPE: PRT
<213> ORGANISM: Artificial Sequence
<220> FEATURE:
<223> OTHER INFORMATION: Synthetic; recombinant polypeptide

<400> SEQUENCE: 24

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Ser Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160
```

```
Thr Glu Leu Pro Ala Gly Leu Leu Asn Gly Leu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
            210                 215                 220

Glu Asn Val Tyr Val Trp Lys Gln Thr Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
                260                 265                 270

Thr Asp Leu Tyr Asp Tyr Tyr Pro Glu Glu Asp Thr Glu Gly Asp Lys
                275                 280                 285

Val Arg Lys Pro Leu Asp Gly Glu Tyr Phe Thr Leu Gln Ile Arg Gly
                290                 295                 300

Arg Glu Arg Phe Glu Met Phe Arg Glu Leu Asn Glu Ala Leu Glu Leu
305                 310                 315                 320

Lys Asp Ala Gln Ala Gly Lys Glu Pro Gly His His His His His His
                325                 330                 335
```

<210> SEQ ID NO 25
<211> LENGTH: 123
<212> TYPE: PRT
<213> ORGANISM: Artificial Sequence
<220> FEATURE:
<223> OTHER INFORMATION: Synthetic; recombinant polypeptide

<400> SEQUENCE: 25

```
Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu
        115                 120
```

<210> SEQ ID NO 26
<211> LENGTH: 290
<212> TYPE: PRT
<213> ORGANISM: Artificial Sequence
<220> FEATURE:
<223> OTHER INFORMATION: Synthetic; recombinant polypeptide

<400> SEQUENCE: 26

```
His Pro Ile Cys Glu Val Ser Lys Val Ala Ser His Leu Glu Val Asn
```

```
            1               5                   10                  15
        Cys Asp Lys Arg Asn Leu Thr Ala Leu Pro Pro Asp Leu Pro Lys Asp
                        20                  25                  30

Thr Thr Ile Leu His Leu Ser Glu Asn Leu Leu Tyr Thr Phe Ser Leu
                        35                  40                  45

Ala Thr Leu Met Pro Tyr Thr Arg Leu Thr Gln Leu Asn Leu Asp Arg
                        50                  55                  60

Ser Glu Leu Thr Lys Leu Gln Val Asp Gly Thr Leu Pro Val Leu Gly
        65                      70                  75                  80

Thr Leu Asp Leu Ser His Asn Gln Leu Gln Ser Leu Pro Leu Leu Gly
                                85                  90                  95

Gln Thr Leu Pro Ala Leu Thr Val Leu Asp Val Ser Phe Asn Arg Leu
                        100                 105                 110

Thr Ser Leu Pro Leu Gly Ala Leu Arg Gly Leu Gly Glu Leu Gln Glu
                        115                 120                 125

Leu Tyr Leu Lys Gly Asn Glu Leu Lys Thr Leu Pro Pro Gly Leu Leu
                        130                 135                 140

Thr Pro Thr Pro Lys Leu Glu Lys Leu Ser Leu Ala Asn Asn Asn Leu
        145                     150                 155                 160

Thr Glu Leu Pro Ala Gly Leu Leu Asn Gly Leu Glu Asn Leu Asp Thr
                        165                 170                 175

Leu Leu Leu Gln Glu Asn Ser Leu Tyr Thr Ile Pro Lys Gly Phe Phe
                        180                 185                 190

Gly Ser His Leu Leu Pro Phe Ala Phe Leu His Gly Asn Pro Trp Leu
                        195                 200                 205

Cys Asn Cys Glu Ile Leu Tyr Phe Arg Arg Trp Leu Gln Asp Asn Ala
                210                 215                 220

Glu Asn Val Tyr Val Trp Lys Gln Thr Val Asp Val Lys Ala Met Thr
        225                     230                 235                 240

Ser Asn Val Ala Ser Val Gln Cys Asp Asn Ser Asp Lys Phe Pro Val
                        245                 250                 255

Tyr Lys Tyr Pro Gly Lys Gly Cys Pro Thr Leu Gly Asp Glu Gly Asp
                        260                 265                 270

Thr Asp Leu Tyr Asp Tyr Tyr Pro Glu Glu Asp Thr Glu Gly Asp Lys
                        275                 280                 285

Val Arg
            290

<210> SEQ ID NO 27
<211> LENGTH: 290
<212> TYPE: PRT
<213> ORGANISM: Artificial Sequence
<220> FEATURE:
<223> OTHER INFORMATION: Synthetic; recombinant polypeptide

<400> SEQUENCE: 27

His Pro Ile Cys Glu Val Ser Lys Val Ala Ser His Leu Glu Val Asn
        1               5                   10                  15

Cys Asp Lys Arg Asn Leu Thr Ala Leu Pro Pro Asp Leu Pro Lys Asp
                        20                  25                  30

Thr Thr Ile Leu His Leu Ser Glu Asn Leu Leu Tyr Thr Phe Ser Leu
                        35                  40                  45

Ala Thr Leu Met Pro Tyr Thr Arg Leu Thr Gln Leu Asn Leu Asp Arg
                        50                  55                  60

Ser Glu Leu Thr Lys Leu Gln Val Asp Gly Thr Leu Pro Val Leu Gly
```

```
                65                  70                  75                  80
        Thr Leu Asp Leu Ser His Asn Gln Leu Gln Ser Leu Pro Leu Leu Gly
                        85                  90                  95

Gln Thr Leu Pro Ala Leu Thr Val Leu Asp Val Ser Phe Asn Arg Leu
                    100                 105                 110

Thr Ser Leu Pro Leu Gly Ala Leu Arg Gly Leu Gly Glu Leu Gln Glu
                    115                 120                 125

Leu Tyr Leu Lys Gly Asn Glu Leu Lys Thr Leu Pro Pro Gly Leu Leu
                130                 135                 140

Thr Pro Thr Pro Lys Leu Glu Lys Leu Ser Leu Ala Asn Asn Asn Leu
        145                 150                 155                 160

Thr Glu Leu Pro Ala Gly Leu Leu Asn Gly Leu Glu Asn Leu Asp Thr
                        165                 170                 175

Leu Leu Leu Gln Glu Asn Ser Leu Tyr Thr Ile Pro Lys Gly Phe Phe
                    180                 185                 190

Gly Ser His Leu Leu Pro Phe Ala Phe Leu His Gly Asn Pro Trp Leu
                    195                 200                 205

Cys Asn Cys Glu Ile Leu Tyr Phe Arg Arg Trp Leu Gln Asp Asn Ala
                210                 215                 220

Glu Asn Val Tyr Val Trp Lys Gln Val Val Asp Val Lys Ala Val Thr
        225                 230                 235                 240

Ser Asn Val Ala Ser Val Gln Cys Asp Asn Ser Asp Lys Phe Pro Val
                        245                 250                 255

Tyr Lys Tyr Pro Gly Lys Gly Cys Pro Thr Leu Gly Asp Glu Gly Asp
                    260                 265                 270

Thr Asp Leu Tyr Asp Tyr Tyr Pro Glu Glu Asp Thr Glu Gly Asp Lys
                    275                 280                 285

Val Arg
            290

<210> SEQ ID NO 28
<211> LENGTH: 11
<212> TYPE: PRT
<213> ORGANISM: Artificial Sequence
<220> FEATURE:
<223> OTHER INFORMATION: Synthetic; recombinant polypeptide

<400> SEQUENCE: 28

Gly Gly Gly Gly Gly Ser Gly Gly Gly Gly Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic; recombinant polypeptide

<400> SEQUENCE: 29

Gly Gly Gly Gly Ser Gly Gly Gly Ser Gly Gly Gly Ser
1               5                   10
```

```
<210> SEQ ID NO 30
<211> LENGTH: 13
<212> TYPE: PRT
<213> ORGANISM: Artificial Sequence
<220> FEATURE:
<223> OTHER INFORMATION: Synthetic; recombinant polypeptide

<400> SEQUENCE: 30

Val Pro Arg Asp Cys Gly Cys Lys Pro Cys Ile Cys Thr
1               5                   10
```

COMPOSITIONS, METHODS AND/OR KITS COMPRISING A RECOMBINANT HUMAN CD38- EXTRACELLULAR DOMAIN

PRIORITY AND CROSS REFERENCE TO RELATED APPLICATIONS

This application is the U.S. National Phase Application under 35 U.S.C. § 371 of International Application No. PCT/IB2018/053939, filed Jun. 1, 2018, designating the U.S., which claims the benefit of U.S. Provisional Application No. 62/543,788, filed Aug. 10, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application includes an electronic Sequence Listing as an ASCII text file submitted via EFS-Web. The electronic Sequence Listing is provided as a file entitled DURC048002APCREPLACEMENTSEQLIST.txt, created and last saved on Oct. 11, 2021, which is 75,750 bytes in size. The information in the electronic Sequence Listing is incorporated herein by reference in its entirety.

BACKGROUND

Field

The present disclosure is related to the field of pharmaceutical products. Some embodiments of the present disclosure relate to compositions, methods and/or kits comprising a soluble recombinant form of CD38-extracellular domain and/or fragments thereof expressed in mammalian cells and/or in bacteria. The present disclosure is also related to fusion proteins comprising an oligomerization tag and methods for oligomerization of recombinant fusion proteins using said tag.

Description of the Related Art

Human CD38 transmembrane protein is highly expressed on certain malignant myeloma. Anti-CD38 monoclonal antibodies are used as therapeutics to kill multiple myeloma and other hematological tumors.

SUMMARY

In some embodiments, a composition for binding to an anti-CD38 antibody is provided. In some embodiments, the composition comprises a recombinant soluble form of an extracellular domain of CD38 and/or a fragment thereof that interferes with a binding activity of an anti-CD38 antibody, wherein a sequence of the recombinant soluble form of the extracellular domain of CD38 and/or the fragment thereof is selected from the group consisting of SEQ ID NO: 7, SEQ ID NO: 8, SEQ ID NO: 9, SEQ ID NO: 10, and SEQ ID NO: 11, SEQ ID NO: 12, SEQ ID NO: 13, and SEQ ID NO: 14.

In some embodiments of the composition, the size of the recombinant soluble form of an extracellular domain of CD38 and/or a fragment thereof ranges from about 5 amino acids to about 300 amino acids.

In some embodiments of the composition, the anti-CD38 antibody is against human CD38, non-human CD38, or a combination thereof.

In some embodiments of the composition, the anti-CD38 antibody is monoclonal, polyclonal, or a combination thereof.

In some embodiments of the composition, the anti-CD38 antibody is selected from the group consisting of Darzalex, isatuximab, and MOR202.

In some embodiments of the composition, the recombinant soluble form of an extracellular domain of CD38 and/or a fragment thereof is expressed in a eukaryotic expression system or a prokaryotic expression system.

In some embodiments of the composition, the concentration of the recombinant soluble form of an extracellular domain of CD38 and/or a fragment thereof ranges from about 1 mg/ml to about 400 mg/ml.

In some embodiments, a kit for bio-monitoring research and diagnostic assays is provided. In some embodiments, the kit comprises a composition comprising a recombinant soluble form of an extracellular domain of CD38 and/or a fragment thereof that interferes with a binding activity of an anti-CD38 antibody, wherein a sequence of the recombinant soluble form of the extracellular domain of CD38 and/or the fragment thereof is selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14, a plate, and reagents for identifying the presence of antibodies.

In some embodiments of the kit, the plate and reagents of the kit are configured for an ELISA assay.

In some embodiments of the kit, the plate and reagents of the kit are those from an assay kit sold under the mark PROMONITOR® as of the filing date of the present application In some embodiments, a method of neutralizing or blocking binding of an anti-CD38 antibody in a sample is provided. In some embodiments, the method of neutralizing or blocking binding of an anti-CD38 antibody comprises providing a volume of the sample comprising the anti-CD38 antibody, and incubating with a volume of the composition according to claim 1 sufficient to neutralize the anti-CD38 antibody in the sample.

In some embodiments of the method of neutralizing or blocking binding of an anti-CD38 antibody, the sample is selected from the group consisting of blood, plasma, and serum.

In some embodiments of the method of neutralizing or blocking binding of an anti-CD38 antibody, the anti-CD38 antibody is selected from the group consisting of Darzalex, isatuximab, and MOR202.

In some embodiments of the method of neutralizing or blocking binding of an anti-CD38 antibody, the volume of the sample ranges from about 25 µl to about 250 µl.

In some embodiments of the method of neutralizing or blocking binding of an anti-CD38 antibody, the volume of the composition ranges from about 0.5 µl to about 50 µl.

In some embodiments of the method of neutralizing or blocking binding of an anti-CD38 antibody, the concentration of the anti-CD38 antibody in the sample ranges from about 0.005 µg/ml to about 2000 µg/ml.

In some embodiments of the method of neutralizing or blocking binding of an anti-CD38 antibody, the concentration of the recombinant soluble form of an extracellular domain of CD38 and/or a fragment thereof in the composition ranges from about 1 mg/ml to about 400 mg/ml.

In some embodiments of the method of neutralizing or blocking binding of an anti-CD38 antibody, the neutralizing effect of the recombinant soluble form of an extracellular domain of CD38 and/or a fragment thereof ranges from about 70% to about 100%.

In some embodiments of the method of neutralizing or blocking binding of an anti-CD38 antibody, the binding activity of anti-CD38 antibody is selected from the group consisting of interference with blood pre-transfusion testing, interference with blood compatibility testing, and interference with antibody therapy.

In some embodiments, a method for selecting a suitable red blood cell unit for a patient treated with anti-CD38 antibodies is provided. In some embodiments, the method for selecting a suitable red blood cell unit comprises obtaining a sample from the patient, said sample being blood or a sample derived from blood of the patient, neutralizing an anti-CD38 antibody in the sample according to the method provided herein of neutralizing or blocking binding of an anti-CD38 antibody in a sample, testing the sample for compatibility with particular red blood cell units, and selecting the red blood cell unit that is compatible with the sample based on the testing.

In some embodiments, a method for removing anti-CD38 in human plasma, serum and/or blood during treatment of the plasma, serum, and/or blood is provided. In some embodiments, the method for removing anti-CD38 comprises exposing the plasma, serum, and/or blood to a composition comprising a recombinant soluble form of an extracellular domain of CD38 and/or a fragment thereof that interferes with a binding activity of an anti-CD38 antibody, wherein a sequence of the recombinant soluble form of the extracellular domain of CD38 and/or the fragment thereof is selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14, wherein the recombinant soluble form of the extracellular domain of CD38 and/or the fragment thereof is tagged with an affinity tag.

In some embodiments of the method for removing anti-CD38, the treatment comprises a treatment selected from the group consisting of hemodialysis, peritoneal dialysis, hemofiltration, hemodiafiltration, plasma exchange therapy and plasmapheresis.

In some embodiments of the method for removing anti-CD38 the affinity tag is selected from the group consisting of Glutathione S-Transferase (GST), small ubiquitin-like modifiers (SUMO), AviTag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, SnoopTag, Biotin Carboxyl Carrier Protein (BCCP), Glutathione-S-transferase-tag, Green fluorescent protein-tag, other fluorescent protein tags, HaloTag, Maltose binding protein-tag, Nus-tag, Thioredoxin-tag, Fc-tag, Designed Intrinsically Disordered tags containing disorder promoting amino acids, Ty tag.

In some embodiments a fusion protein is provided. In some embodiments the fusion protein comprises a recombinant polypeptide fused to an oligomerization tag. In some embodiments the oligomerization tag comprises an immunoglobulin Fc region or a fragment thereof and a polyHis domain.

In some embodiments of the fusion protein, the oligomerization tag is capable of forming higher order of dimers up to 12mer or 6mer of 2mer and possibly higher degree of oligomers.

In some embodiments of the fusion protein, the polyHis domain has between 4 to 24 histidine residues.

In some embodiments of the fusion protein, the polyHis domain has between 6 to 10 histidine residues.

In some embodiments of the fusion protein, the polyHis domain has 6, 8 or 10 histidine residues.

In some embodiments of the fusion protein the sequence of the immunoglobulin Fc region is SEQ ID NO 15. In some embodiments, the sequence of the immunoglobulin Fc region has at least 90% identity to SEQ ID NO 15.

In some embodiments of the fusion protein, the sequence of the recombinant polypeptide and/or the fragment thereof is selected from the group consisting of SEQ ID NO SEQ ID NO 1, SEQ ID NO 25, SEQ ID NO 26, and SEQ ID NO 27.

In some embodiments of the fusion protein, the sequence of the fusion protein and/or the fragment thereof is selected from the group consisting of SEQ ID NO: 7, SEQ ID NO: 12, SEQ ID NO 20, or SEQ ID NO 21.

In some embodiments an oligomerization tag for a recombinant protein is provided. In some embodiments the oligomerization tag comprises an immunoglobulin Fc region or a fragment thereof and a polyHis domain.

In some embodiments of the oligomerization tag for a recombinant protein, the polyHis domain has between 4 to 24 histidine residues.

In some embodiments of the oligomerization tag for a recombinant protein, the polyHis domain has between 6 to 10 histidine residues.

In some embodiments of the oligomerization tag for a recombinant protein, the polyHis domain has 6, 8 or 10 histidine residues.

In some embodiments of the oligomerization tag for a recombinant protein the sequence of the immunoglobulin Fc region is SEQ ID NO 15.

In some embodiments of the oligomerization tag for a recombinant protein the sequence of the immunoglobulin Fc region has at least 90% identity to SEQ ID NO 15.

In some embodiments of the oligomerization tag for a recombinant protein the sequence of the oligomerization tag is selected from the group consisting of SEQ ID NO 5, SEQ ID NO 16, SEQ ID NO 17 and SEQ ID NO 18.

In some embodiments a method for oligomerization of a recombinant fusion protein is provided.

In some embodiments the method for oligomerization of a recombinant fusion protein comprises the steps of:
a) genetically fusing a nucleotide sequence coding for an oligomerization tag according to the present invention to a nucleotide sequence coding for a polypeptide;
b) expressing the resulting nucleotide sequence of step a) in a host cell;
c) purifying the recombinant fusion protein obtained in step b).

BRIEF DESCRIPTION OF THE DRAWINGS

FIG. 2 shows an embodiment of a synthetically designed amino acid encoding recombinant CD38ecd-10H (SEQ ID NO: 8).

FIG. 6 shows an embodiment of the amino acid sequence of CD38 extra-cellular domain (CD38ecd) (SEQ ID NO: 1).

FIG. 7 shows an embodiment of the amino acid sequence of DARA epitopes (SEQ ID NO: 2).

Figure 8:
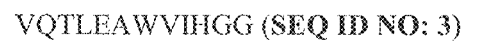

FIG. 8 shows an embodiment of the amino acid sequence of DARA epitope (epitope #1) (SEQ ID NO: 3).

FIG. 9 shows an embodiment of the amino acid sequence of DARA epitope (epitope #2) (SEQ ID NO: 4).

FIG. 10 shows an embodiment of the amino acid sequence of Mouse Fc-10H (SEQ ID NO: 5).

FIG. 11 shows an embodiment of the amino acid sequence of 10H-MBPt (SEQ ID NO: 6).

FIG. 13 shows data related to identification of a low titer anti-D antibody after inhibition of anti-CD38 by CD38ecd-Fc-10H.

DETAILED DESCRIPTION

Recombinant Human CD38ecd

Figure 1:
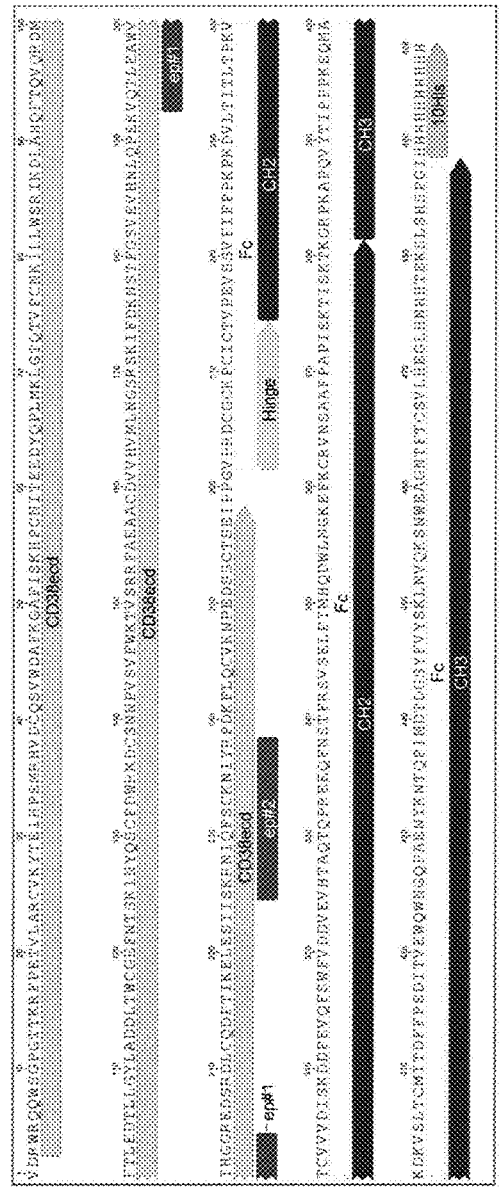
FIG. 1 shows an embodiment of a synthetically designed amino acid encoding recombinant CD38ecd-Fc-10H (SEQ ID NO: 7).

Daratumumab (DARA) is an immunoglobulin (Ig)G1k human monoclonal antibody (mAb) that targets the CD38 transmembrane protein highly expressed on malignant myeloma cells (de Weers M, et al. Daratumumab, a novel therapeutic human CD38 monoclonal antibody, induces killing of multiple myeloma and other hematological tumors. J Immunol. 2011 Feb. 1; 186(3):1840-8; Lokhorst H M, et al. Targeting CD38 with Daratumumab monotherapy in multiple myeloma. N Engl J Med. 2015 Sep. 24; 373(13): 1207-19) and is used for human therapy. In 2016, DARA monotherapy was approved by the Food and Drug Administration (FDA) for the treatment of patients with multiple myeloma who have received at least three prior lines of therapy.

DARA has been reported to interfere with routine blood compatibility tests (Chapuy Cl et al. Resolving the DARA interference with blood compatibility testing. *Transfusion.* 2015 June; 55(6 Pt 2):1545-54; Oostendorp M et al. When blood transfusion medicine becomes complicated due to interference by monoclonal antibody therapy. Transfusion. 2015 June; 55(6 Pt 2):1555-62). DARA specifically recognize endogenous CD38 extracellular domain on the cell surface of red blood cells (RBCs), causing false positive reactions in certain in vitro diagnostic tests.

Plasma samples from DARA-treated patients consistently cause positive reactions in indirect anti-globulin tests (IATs) such as antibody detection (screening) tests, antibody identification panels, and antihuman globulin (AHG) crossmatches. Detection of irregular antibodies in the patient's plasma is masked for up to 6 months after the last DARA infusion. Unexpected/irregular antibodies, like alloantibodies and autoantibodies, are all antibodies that may cause incompatibility in blood transfusions. Irregular antibodies are most commonly of the IgG type. This interference prevents routine pre-transfusion testing and complicates the selection of suitable RBC units for DARA-treated patients. In addition to DARA, two other CD38-specific antibodies (isatuximab and MOR202) are in clinical development and several others are in preclinical development (van de Donk N W, et al. Monoclonal antibodies targeting CD38 in hematological malignancies and beyond. Immunol Rev. 2016 March; 270(1):95-112).

To overcome this problem, different solutions have been developed and reported. Every solution has its own advantages and disadvantages, which are described in Table 1 (Chapuy C.I., et al. DARA-DTT Study Group* for the BEST Collaborative. International validation of a dithiothreitol (DTT)-based method to resolve the daratumumab interference with blood compatibility testing. Transfusion. 2016 December; 56(12):2964-2972).

TABLE 1

Advantages and disadvantages of current anti-CD38 interference mitigation methods.

| Method | Migration mechanism | Advantages | Disadvantages |
|---|---|---|---|
| DTT[5] | Denatures CD38 on reagent cells | Inexpensive<br>Fairly easy<br>DTT commonly used in many blood banks | Must give K– units<br>Always fails to detect antibodies to KEL, DO, IN, JMH, KN, LW<br>Often fails to detect antibodies to: YT, LU, MER2, CROM[12] |
| Trypsin[2] | Cleaves CD38 from reagent cells | Inexpensive<br>Fairly easy<br>Antibodise to KEL group antigens detected | Less commonly used than DTT<br>Always fails to detect antibodies to: Bp[2], Ch/FIG., XG, IN, JMH, M, N, Err[2]TS, Gs[2], Gs4, LU, MER2, KN DO[15] |
| Cord cell antibody screen[2] | Decreased CD38 expression on cord coils | Inexpensive<br>Fairly easy<br>No chemical or enzyme treatment needed. | Not commercially available<br>Not practical for antibody identification<br>Always fails to detect antibodies to: Le[b], Ch/FIG., AnWj, Sd[24]<br>Often fails to detect antibodies to: Le[b] P1, Lu[2], Lu[5],Yl[2], IMH, Kg[x], Vet, Bg, HN, DO, Fyd[12] |
| Soluble CD38[6,7,12] | Anti-CD35 neutralization | Easy<br>No antibodies missed<br>Commercially available<br>Would work with any anti-CD35 | Expensive<br>Short shelf life<br>Additional validation required |

TABLE 1-continued

Advantages and disadvantages of current anti-CD38 interference mitigation methods.

| Method | Migration mechanism | Advantages | Disadvantages |
|---|---|---|---|
| Anti-CD35 idiotype[6,7] | Anti-CD38 neutralization | Easy<br>No antibodies missed | Not commercially available<br>Additional validation required<br>Would need a different anti-idiotype for each manufacturer's anti-CD38 |
| Phenotype matching | Nonserologic method | Commonly performed in blood banks | Rarely, clinically significant antibodies could be missed depending on scent of matening<br>Initial phenotyping should be done before starting anti-CD38<br>Rarely, even with extended matching, additional clinically significant antibody may be produced<br>Availability of matched units and possible extended time to obtain |
| Genotype matching[6] | Nonserologic method | Allows identification of individuals lacking high-frequency antigens (e.g., YP)<br>May be performed after anti-CD38 treatment has begun | Expensive<br>Rarely, genotype results test to correctly predict phenotype<br>Rarely, clinically significant antibodies could be missed depending on extent of matching<br>Rarely even with extended matching, additional clinically significant antibody may be produced<br>Availability of matched units and possible extended time to obtain |

The anti-CD38 neutralization by a soluble form of CD38 extracellular domain and/or a fragment thereof (sCD38ecd, also referred to herein as sCD38) is an attractive method because it does not damage any epitope on the RBC surface, it can neutralize any anti-CD38 antibody, and its implementation in routine lab tests requires just the incubation of the patient's blood, plasma and/or serum sample with sCD38. The main disadvantage is the possible high cost of recombinant sCD38ecd. This disadvantage is subjective because recombinant proteins are widely used for various in vitro diagnostics (IVD) allowing the cost to be kept affordable for routine use. A further possible disadvantage of using sCD38 is the dilution of the patient blood and/or plasma that occurs when neutralizing anti-CD38 using a solution of sCD38, which could lead to missing clinically relevant irregular blood group antibodies in subsequent antibody screening and/or identification. Therefore, it is desirable to have highly concentrated sCD38 available such that only small volumes of sCD38 are required when neutralizing anti-CD38 antibodies in a patient blood and/or plasma sample.

Alternative solutions include the use of chemical denaturants to treat the RBCs which have a very broad and nonspecific effect. Currently, the method of choice for eliminating the DARA interference is DTT treatment of the RBCs causing CD38 to be reduced such that it is not recognized by the DARA antibodies. However this treatment also destroys some other blood group antigens, antibodies to which cannot be detected and identified on the respective cells anymore. For example, treatment of the RBCs in a Reagent Red Blood Cells kit with the reducing agent dithiothreitol (DTT) and redoing the test will effectively negate the binding of DARA to CD38 on the red blood cell surface. However, DTT inactivates and destroys several antigens on the red blood cell surface by disrupting disulfide bonds non-specifically, for example, the Kell system of antigens which are important in blood typing and transfusion reactions.

In contrast, sCD38 does not damage any epitope on the RBC surface and can neutralize any anti-CD38 antibody as long as the sCD38 comprises one or more epitopes that can be bound by the anti-CD38 antibody.

The present disclosure relates to compositions, methods and/or kits comprising recombinant human sCD38 and fragments thereof. The present disclosure also relates to compositions, methods and/or kits comprising recombinant human sCD38 and fragments thereof expressed in eukaryotic and/or prokaryotic expression systems.

In some embodiments, the recombinant sCD38 and/or fragments thereof are solubilized using methods known in the art. In some embodiments, the present inventors have developed a recombinant sCD38 as a blocker to interfere with DARA and/or other anti-CD38 therapeutic antibodies under development. Therefore, in some embodiments, the present disclosure is related to recombinant sCD38 and/or fragments thereof to interfere with one or more antibodies that bind CD38. In some embodiments, recombinant sCD38 and/or fragments thereof interfere with one or more polyclonal antibodies that bind CD38. In some embodiments, recombinant sCD38 and/or fragments thereof interfere with one or more monoclonal antibodies that bind CD38. In some embodiments, recombinant sCD38 and/or fragments thereof interfere with one or more polyclonal and monoclonal antibodies that bind CD38. In some embodiments, recombinant sCD38 and/or fragments thereof interfere with one or more proteins that bind CD38.

In some embodiments, the present disclosure is related to recombinant sCD38 protein and/or fragments thereof to interfere with DARA binding. In some embodiments, recombinant sCD38 and/or fragments thereof interfere with isatuximab binding. In some embodiments, recombinant sCD38 and/or fragments thereof interfere with MOR202 binding. In some embodiments, recombinant sCD38 and/or fragments thereof interfere with one or more of DARA, isatuximab, or MOR202 binding. In some embodiments, the sCD38 and/or a fragment thereof refers to human CD38 protein and/or fragments thereof. In some embodiments, the sCD38 and/or a fragment thereof refers to non-human CD38 protein. Non-limiting examples of non-human sources of CD38 include dogs, cats, rabbit, mouse, guinea pig, monkey, cow, sheep goat, zebra, etc.

In some embodiments, CD38ecd (expressed as sCD38) is as disclosed in FIG. 6. In some embodiments, CD38ecd (expressed as sCD38) is as disclosed in SEQ ID NO: 1. In some embodiments, CD38ecd is a fragment of CD38 protein comprising residues 45 to 300 (SEQ ID NO: 1) of the amino acid sequence human CD38 according to UniProt #P28907. In some embodiments, the CD38ecd is a fragment of the part of CD38 protein predicted to be exposed on a cell surface when expressed naturally on a cell surface. In some embodiments, the CD38ecd is the putative extracellular domain of CD38 protein when naturally expressed on a cell surface.

In some embodiments, the present disclosure is related to expression of CD38ecd (SEQ ID NO: 1) as sCD38, wherein CD38ecd (SEQ ID NO: 1) is part of human CD38 protein predicted to be exposed on a cell surface. In some embodiments, the present disclosure is related to expression of a fragment of CD38ecd (SEQ ID NO: 1) as sCD38, wherein CD38ecd (SEQ ID NO: 1) is part of human CD38 protein predicted to be exposed on a cell surface.

It would be conceivable to one of ordinary skill in the art that recombinant CD38ecd or a fragment thereof can be expressed using one or more expression systems known in the art. Non-limiting examples include bacterial expression systems, and/or eukaryotic expression systems including, but not limited to, insect cells, yeast, and mammalian cell types.

In some embodiments, the expression system is a eukaryotic expression system comprising mammalian cells, yeast cells, insect cells, etc. In some embodiments, the eukaryotic expression system is selected from the group consisting of CHO, HEK, BHK, NSO, Sp2/0, COS, C127, HT-10780, PER.C6, HeLa and/or Jurkat cells. In some embodiments, non-limiting advantages of a eukaryotic expression system (e.g., comprising mammalian cells) related to expression of sCD38 or fragments thereof include correct folding of the sCD38 or a fragments thereof for binding by anti-CD38 antibodies, correct post-translational modifications, proper sorting into the secretory pathway compartments, proper functionality, etc.

In some embodiments, sCD38 is expressed as a fusion protein comprising an immunoglobulin IgG1 Fc region as shown in FIG. 1 (referred to herein as CD38ecd-Fc-10H; SEQ ID NO: 7). In some embodiments, CD38ecd-Fc-10H is a recombinant protein encoded by a synthetically designed nucleic acid encoding a fragment of an immunoglobulin IgG1 constant region. In some embodiments, CD38ecd-Fc-10H is a recombinant protein encoded by a synthetically designed nucleic acid encoding a fragment of an immunoglobulin IgG2 constant region. In some embodiments, CD38ecd-Fc-10H is a recombinant protein encoded by a synthetically designed nucleic acid encoding a fragment of an immunoglobulin IgG3 constant region. In some embodiments, CD38ecd-Fc-10H is a recombinant protein encoded by a synthetically designed nucleic acid encoding a fragment of an immunoglobulin IgG4 constant region. In some embodiments, CD38ecd-Fc-10H is a recombinant protein encoded by a synthetically designed nucleic acid encoding a fragment of an immunoglobulin of any of the above IgG isotypes of constant region with an altered hinge region so that a monomeric Fc-fusion is expressed. In some embodiments, CD38ecd-Fc-10H comprises CD38ecd fused onto the N-terminus of SEQ ID NO: 5 (FIG. 10) comprising a fragment of an immunoglobulin IgG constant region comprising of a hinge region, a CH2 domain and a CH3 domain, which is fused at the C-terminus to a 10 histidine tag and a stop codon. In some embodiments, CD38ecd-Fc-10H is expressed on a cell surface. In some embodiments, the murine IgG1 constant region improves one or more of expression, solubility, and stability of an expressed protein. In some embodiments, the murine IgG1 constant region improves one or more of expression, solubility, and stability of a cell-surface expressed protein. In some embodiments, the His tag allows for purification of CD38ecd-Fc-10H by Immobilized Metal Affinity Chromatography (IMAC) purification.

As used herein, "nucleic acid" can be DNA-based, RNA-based, or a combination thereof. Non-limiting examples include plasmids, cosmids, phage viral vectors, adeno viral vectors, minicircles, modified nucleic acids, nucleic acid analogs, etc. that are well-known in the art. In some embodiments, a nucleic acid is designed for efficient expression of a protein, a peptide, or both in a eukaryotic expression system, a prokaryotic expression system, or both. Also encompassed are vaccines vectors based on nucleic acids. Non-limiting examples include DNA vaccine vectors, RNA vaccine vectors, virus-based vaccine vectors (e.g., adeno-associated virus-based vaccine vectors), etc.

Without being bound by any theory, it is believed in the art that the natural state for CD38 in a membrane is dimeric and/or tetrameric (Bruzzone S et al. Dimeric and tetrameric forms of catalytically active transmembrane CD38 in transfected HeLa cells. *FEBS Lett.* 1998 Aug. 21; 433(3):275-8). In some embodiments, CD38ecd-Fc-10H is expressed as a dimeric protein. In some embodiments, the dimeric protein is a homodimer of CD38ecd-Fc-10H. In some embodiments, CD38ecd-Fc-10H may be expressed as an oligomeric protein comprising more than two copies of CD38ecd-Fc-10H. In some embodiments, CD38ecd-Fc-10H is expressed as an oligomeric protein. In some embodiments, CD38ecd-Fc-10H is expressed as an oligomeric protein comprising from two copies of CD38ecd-Fc-10H to 12 copies of CD38ecd-Fc-10H. In some embodiments, the His tag allows for purification of CD38ecd-Fc-10H by IMAC purification.

In some embodiments, sCD38 is expressed as a fusion protein as shown in FIG. 2 (referred to herein as CD38ecd-10H; SEQ ID NO: 8). In some embodiments, CD38ecd-10H is a recombinant protein encoded by a synthetically designed nucleic acid encoding CD38ecd with a His tag (i.e., a tag comprising histidine residues). In some embodiments, the His tag allows for purification of CD38ecd-10H by IMAC purification.

In some embodiments, the activity of the oligomeric CD38ecd-Fc-10H is better than the activity of the monomeric CD38ecd-10H in solution, on a solid surface, or both. In some embodiments, "activity" refers to the ability of sCD38 to neutralize an anti-CD38 antibody. In some embodiments, "activity" refers to the ability of sCD38 to neutralize one or more effects related to anti-CD38 antibody on a solid surface or in solution or both. In some embodiments, the efficacy/efficiency of the "activity" ranges from about >70% to about 100%. In some embodiments, the efficacy/efficiency of the "activity" is about 70, 75, 80, 85, 90, 95, 96, 97, 98, 99, or 100%, or a value within a range defined by any two of the aforementioned values. In some embodiments, the efficacy/efficiency of the "activity" ranges from about >90% to 100%. In some embodiments, the efficacy/efficiency of the "activity" is about >90, 91, 92, 93, 94, 95, 96, 97, 98, 98.5, 99, 99.5, or 100%, or a value within a range defined by any two of the aforementioned values.

Figure 3:
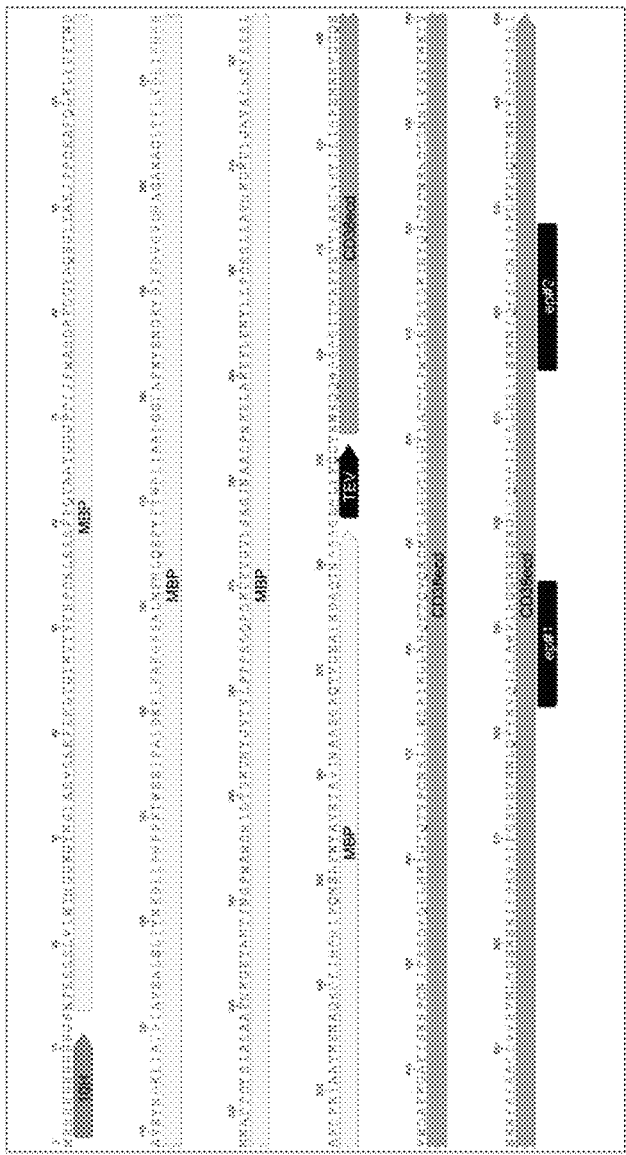
FIG. 3 shows an embodiment of a synthetically designed amino acid encoding recombinant 10H-MBPt-CD38ecd (SEQ ID NO: 9).

In some embodiments, sCD38 is expressed in a bacterial expression system. In some embodiments, non-limiting advantages of a bacterial expression system include lower cost yet maintenance of the functionality of a eukaryotic protein. In some embodiments, the expression system is a bacterial expression system. In some embodiments, sCD38 is expressed as a fusion protein as shown in FIG. 3 (referred to herein as 10H-MBPt-CD38ecd; SEQ ID NO: 9). In some embodiments, 10H-MBPt-CD38ecd is a recombinant protein encoded by a synthetically designed nucleic acid encoding CD38ecd fused at its N-terminus to a 10H-MBPt tag (SEQ ID NO: 6; FIG. 11, or SEQ ID NO: 19) comprising 10 histidine residues and the entire bacterial Maltose Binding Protein (MBP) (Uniprot #P0AEX9; amino acid residues 29 to 393). In some embodiments, the 10 histidine tag is used for IMAC purification. In some embodiments, the MBP improves one or more of expression, solubility, or folding.

In some embodiments, 10H-MBPt-CD38ecd comprises a Tobacco Etch Virus (TEV) protease cleavage sequence. In some embodiments, 10H-MBPt-CD38ecd comprises a TEV protease cleavage sequence between MBP and CD38ecd (FIG. 3). In some embodiments, the TEV protease cleavage sequence between MBP and CD38ecd allows for cleaving off 10H-MBP from CD38ecd resulting in purified CD38ecd without any additional sequences.

One or more other protease and non-protease cleavage sites are also contemplated. Non-limiting examples include foot-and-mouth disease virus (FMDV) protease, Arg-C proteinase, Asp-N endopeptidase, BNPS-Skatole, Caspases, Chymotrypsin-high specificity, Chymotrypsin-low specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, LysN, NTCB (2-nitro-5-thiocyanobenzoic acid), Neutrophil elastase, Pepsin, Proline-endopeptidase, Proteinase K, Staphylococcal peptidase I, Thermolysin, Thrombin, Trypsin, and other site specific enzymes known to one of ordinary skill in the art.

Figure 4:
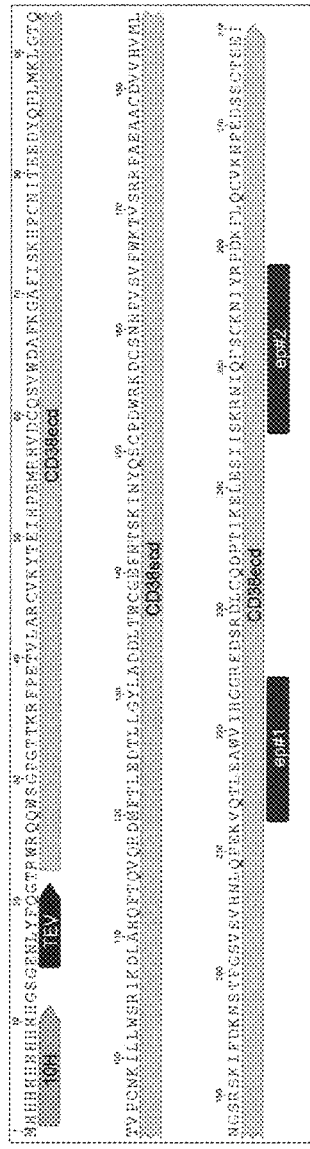
FIG. 4 shows an embodiment of a synthetically designed amino acid encoding recombinant 10Ht-CD38ecd (SEQ ID NO: 10).

In some embodiments, sCD38 is expressed as a fusion protein as shown in FIG. 4 (referred to herein as 10Ht-CD38ecd; SEQ ID NO: 10). In some embodiments, 10Ht-CD38ecd is a recombinant protein encoded by a synthetically designed nucleic acid encoding CD38ecd fused at its N-terminus with a tag comprising 10 histidine residues. In some embodiments, the 10 histidine tag is used for IMAC purification. In some embodiments, 10H-CD38ecd comprises a Tobacco Etch Virus (TEV) protease cleavage sequence. In some embodiments, 10H-CD38ecd comprises a TEV protease cleavage sequence between 10H and CD38ecd (FIG. 4). In some embodiments, the TEV protease cleavage sequence between 10H and CD38ecd allows for cleaving off 10H from CD38ecd resulting in purified CD38ecd without any additional sequences.

Figure 5:
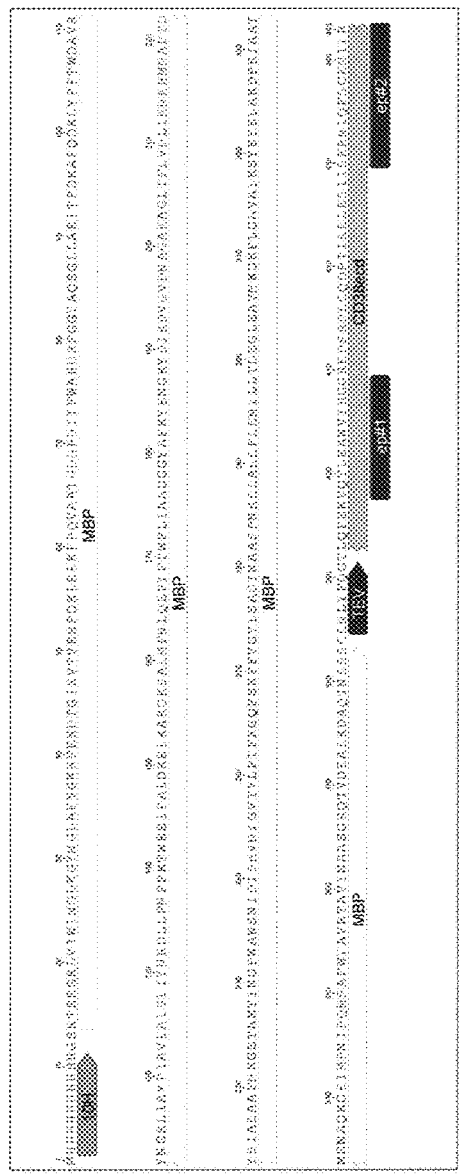
FIG. 5 shows an embodiment of a synthetically designed amino acid encoding recombinant 10H-MBPt-DARAepitopes (SEQ ID NO: 11).
Figure 12:
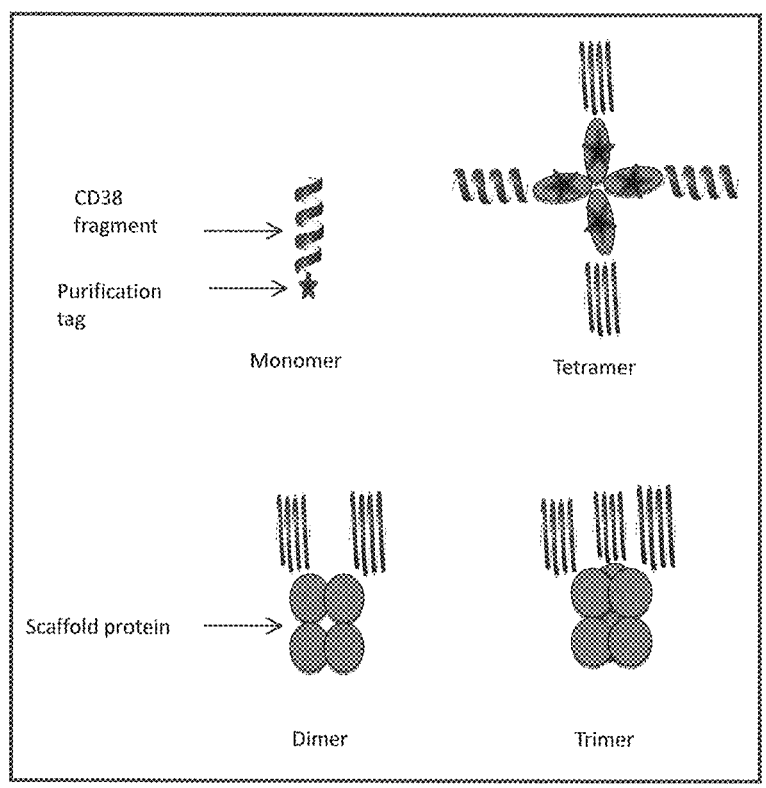
FIG. 12 depicts a schematic of the various recombinant CD38 proteins using alternative scaffolds.

In some embodiments, sCD38 is expressed as a fusion protein as shown in FIG. 5 (referred to herein as 10H-MBPt-DARAepitopes; SEQ ID NO: 11). In some embodiments, 10H-MBPt-DARAepitopes is a recombinant protein encoded by a synthetically designed nucleic acid encoding comprising the amino acid sequence (from residues 230 to 280 of Uniprot #P28907; as shown in SEQ ID NO: 2) of human CD38 comprising two DARA epitopes fused at its N-terminus with a 10 Histidines tag and the Maltose Binding Protein as shown in FIG. 5. In some embodiments, the two DARA epitopes are epitopes are DARAepitope #1 (Uniprot #P28907 from residues 235 to 246; as shown in SEQ ID NO: 3) and DARAepitope #2 (Uniprot #P28907 from residues 267 to 280; as shown in SEQ ID NO: 4).

In some embodiments, one or more epitopes of sCD38 can bind an anti-CD38 antibody with a measurable affinity of about 10e-6 (peptide affinity) to 10e-10 (very strong antibody affinity).

In some embodiments, a 10 histidine tag is used for IMAC purification. In some embodiments, 10H-MBPt-DARAepitopes comprises a Tobacco Etch Virus (TEV) protease cleavage sequence. In some embodiments, 10H-MBPt-DARAepitopes comprises a TEV protease cleavage sequence between MBP and DARAepitopes (FIG. 5). In some embodiments, the TEV protease cleavage sequence between MBP and DARAepitopes allows for cleaving off 10H-MBP from DARAepitopes resulting in purified DARAepitopes without any additional sequences. In some embodiments, the MBP improves one or more of expression, solubility, or folding.

In some embodiments, the fragment of sCD38 is one or more epitopes in CD38ecd that are bound by one or more anti-CD38 polyclonal and/or monoclonal antibodies. In some embodiments, the size of the sCD38 and/or the fragment thereof ranges from about 5 amino acids to about 300 amino acids. In some embodiments, the size ranges from about 10 to about 150 amino acids. In some embodiments, the size is about 5, 10, 25, 50, 100, 150, 200, 250, 300 or 350 amino acids, or a value within a range defined by any two of the aforementioned values.

One or more other tags for purification, solubilization, detection, etc. are also contemplated. Non-limiting examples include GST, SUMO, AviTag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, SnoopTag, BCCP (Biotin Carboxyl Carrier Protein), Glutathione-S-transferase-tag, Green fluorescent protein-tag, other fluorescent protein tags, HaloTag, Maltose binding protein-tag, Nus-tag, Thioredoxin-tag, Fc-tag, Designed Intrinsically Disordered tags containing disorder promoting amino acids (e.g., P, E, S, T, A, Q, G), Ty tag, etc.

The present disclosure is related to one or more compositions, methods and/or kits comprising any one or more of the embodiments of sCD38 and/or fragments thereof described herein and variants thereof.

In some embodiments, one or more compositions, methods and/or kits comprising sCD38 and/or fragments thereof relate to a universal blood, serum and/or plasma pretreatment. In some embodiments, the pretreatment mitigates any interference by anti-CD38 antibody in the sample in the detection and/or identification of irregular antibodies as well as other antibodies by one or more techniques known to one of ordinary skill in the art.

In some embodiments, interference by an anti-CD38 antibody comprises one or more of interference with blood compatibility testing, interference with antibody therapy, agglutination of red blood cells, interference with blood pre-transfusion testing, and the like.

In some embodiments, the pretreatment neutralizes any anti-CD38 antibody to allow for detection and/or identification of irregular antibodies as well as other antibodies by one or more techniques known to one of ordinary skill in the art in the sample. Non limiting of examples one or more techniques known to one of ordinary skill in the art include conventional tube testing, multicard, solid-phase red-cell adherence tests, gel technologies, any other current or future technologies for the detection/identification of irregular antibodies.

Mitigation of interference by and/or neutralization of anti-CD38 antibodies by pretreatment allow for detection and/or identification of irregular antibodies as well as other antibodies that are relevant and important for compatibility testing. Therefore, in some embodiments, neutralization by sCD38 and/or fragments thereof of anti-CD38 in a plasma, blood and/or serum sample can be combined with diagnostics uses, for example, antibody screening, identification of irregular blood group antibodies, etc.

In some embodiments, sCD38 and/or fragments thereof can be used as a pretreatment reagent in blood screening, plasma screening, serum screening, or a combination thereof for irregular antibodies as well as other antibodies. In some embodiments, sCD38 and/or fragments thereof can be used as an antigen in bio-monitoring research and diagnostic assays. For example, in some embodiments, sCD38 and/or fragments thereof can be used in PROMONITOR® ELISA to test for drug bioavailability and immunogenicity, for example, of anti-CD38 antibodies such as DARA, isatuximab, or MOR202, in patients prescribed with biological therapy for the treatment of chronic inflammatory diseases and other indications (e.g., multiple myeloma). In some embodiments, sCD38 can be used for PROMONITOR® family of tests to measure both drug levels and anti-drug antibodies levels with validated ELISA.

In some embodiments, the efficacy of mitigation of interference by and/or neutralization of anti-CD38 antibodies by pretreatment can be tested using one or more techniques known to one of ordinary skill in the art. For example, in some embodiments, one or more compositions provided herein can be used in DG Gel®, a unique 8-column gel card based on column agglutination technology for blood group typing and investigation of unexpected antibodies. Thus, in some embodiments, the compositions provided herein can be used as a reagent in DG Gel® cards to test the efficiency of anti-CD38 neutralization. In some embodiments, the efficacy ranges from about >70% to about 100%. In some embodiments, the efficacy is about 70, 75, 80, 85, 90, 95, 96, 97, 98, 99, or 100%, or a value within a range defined by any two of the aforementioned values. In some embodiments, the efficacy ranges from about >90% to 100%. In some embodiments, the efficacy is about >90, 91, 92, 93, 94, 95, 96, 97, 98, 98.5, 99, 99.5, or 100%, or a value within a range defined by any two of the aforementioned values. In some embodiments, the volume of one or more compositions comprising sCD38 used in DG Gel® cards can range from about 0.1 µl to about 40 µl. In some embodiments, the volume of compositions comprising sCD38 used in DG Gel® cards can range from about 0.4 µl to about 10 µl. In some embodiments, the volume of composition comprising sCD38 used in DG Gel® cards is about 2 µl.

In some embodiments, the compositions provided herein can be used in assays to block and/or neutralize one or more of DARA, isatuximab, or MOR202 in patient blood, serum, and/or plasma samples.

In some embodiments, the compositions, methods and/or kits provided herein can be used in assays to remove one or more anti-CD38 antibodies from patient blood, serum, and/or plasma samples. For example, a patient sample comprising anti-CD38 antibody can be incubated with a composition comprising sCD38 and/or fragments thereof comprising one or more tags disclosed herein to allow the tagged sCD38 and/or fragments thereof to bind the anti-CD38 antibody. The sCD38-anti-CD38 complex can then be removed by one or more affinity chromatography techniques known to one of ordinary skill in the art.

In some embodiments, a tagged sCD38 and/or fragments thereof can be used to remove anti-CD38 in human plasma, serum and/or blood during hemodialysis, peritoneal dialysis, hemofiltration, hemodiafiltration, plasma exchange therapy, plasmapheresis, apheresis, and leukoreduction. For example, a tagged sCD38 and/or fragments thereof can be used to remove one or more of DARA, isatuximab, or MOR202 in patient blood, serum, and/or plasma samples.

In some embodiments, a concentration range of anti-CD38 antibody in a sample ranges from about 0.005 µg/ml to about 2000 µg/ml. In some embodiments, a concentration range of anti-CD38 antibody in a sample ranges from about 0.05 µg/ml to about 1000 µg/ml. In some embodiments, a concentration range of anti-CD38 antibody in a sample ranges from about 0.05 µg/ml to about 500 µg/ml. In some embodiments, a concentration range of anti-CD38 antibody in a sample ranges from about 0.05 µg/ml to about 20 µg/ml. In some embodiments, a concentration range of anti-CD38 antibody in a sample ranges from about 0.05 µg/ml to about 100 µg/ml. In some embodiments, a concentration range of anti-CD38 antibody in a sample ranges is about 0.005, 0.05, 0.1, 0.25, 0.5, 1, 5, 25, 50, 75, 100, 150, 250, 300, 400, 500, 750, 1000, 1500 or 2000 µg/ml, or a value within a range defined by any two of the aforementioned values. In other embodiments, a concentration range of anti-CD38 antibody in a sample ranges from about 0.05 µg/ml to about 2000 µg/ml.

In some embodiments, the volume of one or more compositions comprising sCD38 and/or fragments thereof used in the methods and/or kits disclosed herein can range from about 0.05 µl to about 50 µl. In some embodiments, the volume of one or more compositions comprising sCD38 and/or fragments thereof used in the methods and/or kits disclosed herein can range from about 0.25 µl to about 10 µl. In some embodiments, the volume of one or more compositions comprising sCD38 used in the methods and/or kits disclosed herein is about 2 µl.

In some embodiments, the volume of a sample (e.g., blood, plasma, serum, etc.) can range from about 1 µl to about 100 µl. In some embodiments, the volume of a sample (e.g., blood, plasma, serum, etc.) can range from about 100 µl to about 5 ml. In some embodiments, the volume of a sample (e.g., blood, plasma, serum, etc.) can range from about 5 ml to about 500 ml. In some embodiments, the volume of a sample (e.g., blood, plasma, serum, etc.) can range from about 250 ml to about 10,000 ml. In some embodiments, the volume of a sample (e.g., blood, plasma, serum, etc.) can range from about 25 µl to about 250 µl.

In some embodiments, the concentration of sCD38 and/or fragments thereof in the compositions provided herein ranges from about 0.25 mg/ml to about 400 mg/ml. In some embodiments, the concentration of sCD38 and/or fragments thereof in the compositions and compositions in kits thereof provided herein ranges from about 4 mg/ml to about 100 mg/ml. In some embodiments, the concentration of sCD38 and/or fragments thereof in the compositions provided herein ranges is about 0.25, 0.5, 1, 2.5, 5, 7.5, 10, 15, 20, 25, 30, 50, 75, 100, 125, 150, 175, 200, 225, 250, 275, 300, 325, 350, 375 or 400 mg/ml, or a value within a range defined by any two of the aforementioned values. In some embodiments, the concentration of sCD38 and/or fragments thereof in the compositions provided herein is about 20 mg/ml.

In some embodiments, a concentration range of sCD38 and/or fragments thereof for optimal inhibition of anti-CD38 ranges from about 1 mg/ml to about 500 mg/ml. In some embodiments, a concentration range of sCD38 and/or fragments thereof for optimal inhibition of anti-CD38 ranges from about 5 mg/ml to about 100 mg/ml.

In some embodiments, the stability of the embodiments of sCD38 and/or fragments thereof according to the present disclosure ranges from about 30 days to about 300 days at 37° C. In some embodiments, the stability of sCD38 and/or fragments thereof ranges from about 6 months to about 48 months at 2 to 8° C.

In some embodiments, the compositions disclosed herein can be provided in the form of one or more kits.

In some embodiments, the compositions and compositions in kits thereof are provided in liquid, solid, or semi-solid form. Non-limiting examples include capsule, tablet, ovule, insert, wafer, granule, pellet, bead, pill, sachet, sprinkle, film, cream, gel, syrup, reconstitutable solid, suspension, emulsion, troche, powder, triturate, platelet, etc.

In some embodiments, the compositions and compositions in kits thereof comprise active ingredients, inactive ingredients, excipients, additives, and/or pharmaceutically acceptable carriers. Non-limiting examples include polymer compounds, inorganic salts, amino acids (non-limiting examples include arginine, histidine, proline etc.), binders, lubricants, disintegrants, surfactants, thickeners, coating agents, pH adjusters, antioxidants, flavoring agents, preservatives, colorants, etc. Non-limiting examples of other pharmaceutically acceptable carriers include liquid carriers such as water, alcohol, emulsion, and solid carriers such as gel, powder, etc. In some embodiments, the compositions and compositions in kits thereof may comprise appropriate salts and buffers to render deliver vehicles stable and allow for uptake by target cells.

In some embodiments, pharmaceutically acceptable carriers may include one or more solvents, buffers, solutions, dispersion media, coatings, antibacterial and antifungal agents, metal chelators (e.g., EDTA), isotonic and absorption delaying agents and the like.

Aqueous compositions and compositions in kits thereof comprise an effective amount of sCD38 and/or fragment thereof (e.g., as protein, nucleic acid, or both) in a delivery vehicle (e.g. liposomes, nanoparticles, or other complexes), dissolved or dispersed in a pharmaceutically acceptable carrier or aqueous medium. Other excipients include water soluble polymer, water insoluble polymers, hydrophobic materials, hydrophilic materials, waxes, disintegrants, superdisintegrants, diluents, binders, etc.

As used herein, the term "subject" or "patient" refers to any vertebrate including, without limitation, humans, non-human primates, cattle, sheep, pigs, goats, horses, dogs, cats, mice, rats, guinea pigs, chicken, turkey, ducks, geese. In some embodiments, the subject is a mammal. In some embodiments, the subject is a human. In some embodiments, the subject is a male or a female.

Oligomerization Tag for Fusion Proteins

The present disclosure also relates to fusion proteins comprising an oligomerization tag and methods for oligomerization of a recombinant fusion protein. The present disclosure also relates to oligomerization tags for recombinant fusion proteins comprising an immunoglobulin Fc region or a fragment thereof and a polyHis domain.

Fusion proteins may optionally be fused to an oligomerization tag for the formation of oligomers such as dimers, trimers, tetramers, pentamers, and/or higher-order oligomers. An oligomerization tag may favor a specific stoichiometry, e.g., dimers, trimers, tetramers, or pentamers, or an oligomerization tag may allow for a distribution of oligomers having different stoichiometries. An oligomerization tag may be designed to form homo-oligomers, although the distinction between homo-oligomers and hetero-oligomers is not particularly limiting. In some embodiments, the oligomerization tag is capable of forming a homo-dimer, homo-trimer, homo-tetramer, or homo-pentamer, e.g., wherein the oligomerization of a recombinant polypeptide results in a predominantly monodisperse oligomer. An oligomerization tag provides several advantages for fusion proteins that are used in assays. An oligomerization tag can orient recombinant polypeptides relative to each other. An oligomerization tag can also increase the affinity of a recombinant polypeptide for a target. An oligomerization tag can also increase the avidity of a recombinant polypeptide which refers to the functional accumulation of affinity with multiple binding groups.

In some embodiments, the fusion protein comprises a recombinant polypeptide fused to an oligomerization tag. In some embodiments, the sequence of the recombinant polypeptide and/or the fragment thereof is selected from the group consisting of SEQ ID NO 1, SEQ ID NO 25, SEQ ID NO 26, and SEQ ID NO 27. In some embodiments, the oligomerization tag comprises an immunoglobulin Fc region or a fragment thereof and a polyHis domain. In some embodiments, the sequence of the fusion protein and/or the fragment thereof is selected from the group consisting of SEQ ID NO: 7, SEQ ID NO: 12, SEQ ID NO 20, and SEQ ID NO 21.

In some embodiments the polyHis domain is a purification domain fused to a recombinant protein. In some embodiments the polyHis domain is an affinity tag fused to a recombinant protein. In some embodiments, the polyHis domain is an oligomerization tag fused to a recombinant protein. In some embodiments, the polyHis domain is comprised within an oligomerization tag together with other domains. In some embodiments, the polyHis domain is comprised within an oligomerization tag together with an immunoglobulin Fc region or a fragment thereof. A polyHis domain according to the embodiments herein typically contains between 2 to 24 histidine residues. In some embodiments, the polyHis domain contains between 6 to 12 histidine residues. A polyHis domain according to the embodiments herein typically contains 6, 7, 8, 9, 10, 11 or 12 histidine residues.

In some embodiments, the fusion protein herein is expressed fused to an oligomerization tag comprising an immunoglobulin Fc region or a fragment thereof. In some embodiments the oligomerization tag includes the amino acid sequence of an immunoglobulin Fc domain hinge region. In some embodiments, the fusion protein herein is expressed fused to an oligomerization tag comprising an immunoglobulin Fc region or a fragment thereof. In some embodiments, the oligomerization tag comprises an immunoglobulin IgG1 constant region. In some embodiments, the oligomerization tag comprises an immunoglobulin IgG2 constant region. In some embodiments, the oligomerization tag comprises an immunoglobulin IgG3 constant region. In some embodiments, the oligomerization tag comprises an immunoglobulin IgG4 constant region. In some embodiments, the oligomerization tag comprises a fragment of an immunoglobulin of any of the above IgG isotypes of constant region with an altered hinge region so that a monomeric Fc-fusion is expressed. In some embodiments, the oligomerization tag comprises a fragment of an immunoglobulin IgG constant region comprising a hinge region, a CH2 domain and a CH3 domain, which is fused at the C-terminus to a polyHis domain and a stop codon.

The species of an immunoglobulin Fc domain may be selected based on the desired use of a fusion protein. For example, the species of immunoglobulin Fc domain may be selected such that a specific reagent either targets or ignores the immunoglobulin Fc domain in an assay. A mouse Fc domain may be useful, for example, if no anti-mouse secondary antibody is used to detect other mouse antibodies in an assay. Similarly, a mouse Fc domain may be useful to cross-link a fusion protein to a solid support or other component of an assay using an anti-mouse antibody. The species of Fc domain may be human, mouse, rabbit, rat, hamster, guinea pig, goat, sheep, horse, chicken, or a chimera of any of the foregoing species, although the species of Fc domain is not particularly limiting.

An exemplary oligomerization tag is the mouse IgG Fc domain comprising the hinge region, which allows for recombinant polypeptides comprising the oligomerization tag to form a covalent homodimer.

In some embodiments, the amino acid sequence of the Fc region of the oligomerization tag is SEQ ID NO 15. In some embodiments, the sequence of the immunoglobulin Fc region has at least 90% identity to SEQ ID NO 15. In some embodiments, the sequence of the immunoglobulin Fc region has between 90% and 100% identity to SEQ ID NO 15. In some embodiments, the sequence of the immunoglobulin Fc region has at least 90%, at least 95% or at least 98% identity to SEQ ID NO 15.

In addition to the benefits of oligomerization tags described above, Fc domains often increase the expression and/or secretion of a recombinant polypeptide in expression cells.

Fc domains may also aid the purification of a recombinant polypeptide as methods of purifying polypeptides comprising Fc domains are well known.

Other oligomerization tags are known in the art, and the specific choice of oligomerization tag is not particularly limiting. In some embodiments, the fusion protein herein comprises a recombinant polypeptide and/or a fragment thereof. In some embodiments, the recombinant polypeptide and/or the fragment thereof is any protein of interest that can be fused to an oligomeriation tag according to the present invention. In some embodiments, the recombinant polypeptide is a recombinant soluble form of an extracellular domain of CD38 or a fragment thereof. In some embodiments the recombinant polypeptide is a modified extracellular domain of CD47 or a fragment thereof. In some embodiments the recombinant polypeptide is a modified extracellular domain of platelet glycoprotein Ibα (Gplbα) or a fragment thereof. In some embodiments, the sequence of the recombinant polypeptide and/or the fragment thereof is selected from the group consisting of SEQ ID NO 1, SEQ ID NO 25, SEQ ID NO 26, and SEQ ID NO 27.

In some embodiments, the sequence of the oligomerization tag is selected from the group consisting of SEQ ID NO 5, SEQ ID NO 16, SEQ ID NO 17 and SEQ ID NO 18.

In some embodiments, the oligomerization tag further comprises a region or domain with a sequence selected from the group consisting of SEQ ID NO 28, SEQ ID NO 29, and SEQ ID NO 30.

The present disclosure also relates to methods for oligomerization of a recombinant fusion protein. In some embodiments, the methods for oligomerization of a recombinant fusion protein comprises the steps of: a) genetically fusing a nucleotide sequence coding for an oligomerization tag according to the embodiments of the present disclosures to a nucleotide sequence coding for a polypeptide; b) expressing the resulting nucleotide sequence of step a) in a host cell; c) purifying the recombinant fusion protein obtained in step b).

In some embodiments, the oligomerization tag used in the method for oligomerization of a recombinant fusion protein comprises an immunoglobulin Fc region or a fragment thereof and a polyHis domain. In some embodiments, the polyHis domain contains between 2 to 24 histidine residues.

In some embodiments, the polyHis domain contains between 6 to 12 histidine residues. A polyHis domain according to the embodiments herein typically contains 6, 7, 8, 9, 10, 11 or 12 histidine residues. In some embodiments, the amino acid sequence of the Fc region of the oligomerization tag used in the method for oligomerization of a recombinant fusion protein is SEQ ID NO 15. In some embodiments, the sequence of the immunoglobulin Fc region has at least 90% identity to SEQ ID NO 15. In some embodiments, the sequence of the immunoglobulin Fc region has between 90% and 100% identity to SEQ ID NO 15. In some embodiments, the sequence of the immunoglobulin Fc region has at least 90%, at least 95% or at least 98% identity to SEQ ID NO 15.

In some embodiments, the sequence of the oligomerization tag used in the method for oligomerization of a recombinant fusion protein is selected from the group consisting of SEQ ID NO 5, SEQ ID NO 16, SEQ ID NO 17 and SEQ ID NO 18.

In some embodiments, the oligomerization tag used in the method for oligomerization of a recombinant fusion protein further comprises a region or domain with a sequence selected from the group consisting of SEQ ID NO 28, SEQ ID NO 29, and SEQ ID NO 30.

In some embodiments, the sequence of the recombinant fusion protein obtained in step c) of the method for oligomerization of a recombinant fusion protein disclosed herein is selected from the group consisting of SEQ ID NO: 7, SEQ ID NO: 12, SEQ ID NO 20, and SEQ ID NO 21.

EXAMPLES

The following Examples are non-limiting and other variants contemplated by one of ordinary skill in the art are included within the scope of this disclosure.

Example 1

Multiple versions of the CD38 protein were constructed to attempt to recreate the correct folding of the CD38ecd and to block a therapeutic mAb from causing problems in the detection of irregular antibodies assay. One version was monomeric extracellular domain fused to an affinity tag (CD38ecd-10His). A second version, CD38ecd-Fc fusion, CD38ecd was fused to a murine Fc region (hinge-CH2-CH3) which thereby creates dimeric versions (doublet) held together by the Fc region. In another version, CD38ecd-Fc-10H fusion, CD38ecd was fused to an oligomeric tag, which thereby creates multimeric versions. In another version, CD38ecd-Clath, CD38ecd was fused to a clathrin domain. The clathrin domain allowed for trimerization. Another version, CD38ecd-p53, involved fusing to a p53 domain. The p53 domain is known to cause tetramerization. In all cases these are novel compositions not found in nature. The versions were expressed in mammalian cells in order to preserve any post-translational modifications essential for maintaining CD38 function.

Example 2

A recombinant CD38 protein is sold by several companies for research use. However, the amount and cost of commercially available CD38 price is prohibitive for many purposes. Attempts by other companies to produce recombinant CD38 are fraught with issues, including the problems of solubility, achieving high concentration, and epitope avidity through scaffolding, and none of these commercially available CD38 proteins has the composition of the CD38 proteins and/or fragments thereof as provided herein.

Initial tests with the expression systems described herein show that CD38ecd-Fc-10H was soluble and functional. Importantly, the recombinant CD38ecd-Fc-10H was soluble at high concentrations (up to 35 mg/ml) allowing the use of as little as 2 µl of the concentrated solution of CD38ecd Fc in DG Gel® cards.

Example 3—Anti-CD38 Titers in Patient Samples

The goal of this experiment was to establish the minimum amount of CD38ecd-Fc-10H protein required to inhibit and fully neutralize broadly anti-CD38 antibody of unknown concentration and titer found in patient plasma samples, in order to completely eliminate the effect of anti-CD38 antibody. Plasma of three patients after treatment with anti-CD38 were titrated in an Indirect Antiglobulin Test (IAT) with a commercial Reagent Red Blood Cell for Antibody Screening. The experiment was performed as follows: Plasma Titration: 75 µl of anti-CD38 containing plasma of each patient was arithmetically titrated in PBS, pH 7.4 until 1:8192.

Antibody Screening: 50 µl of one cell of Screen-Cyte 0.8% (Medion Grifols Diagnostics, Duedingen, Switzerland) and 25 µl of the respective plasma titer were pipetted in the incubation chamber of a microcolumn in a DG Gel Coombs Card (Diagnostic Grifols, Barcelona, Spain) and incubated for 15 min at 37° C. The Card was then centrifuged in a centrifuge for DG Gel cards and the results read.

The established titers ranged between 1:1 and 1:4096. It was concluded that for an effective pretreatment of patient plasma with sCD38, a titer of anti-CD38 of at least 1:2048, better 1:8192, had to be neutralized.

Example 4—sCD38 Inhibits Anti-CD38 Antibodies

Example 4a: Inhibition using a preparation containing 2.2 mg/ml CD38ecd-Fc-10H Sample preparation (inhibition test): 25 µl of plasma from patient 1 containing anti-CD38, non-diluted or arithmetically titrated in PBS, pH 7.4, was incubated with 2 µl to 32 µl of a preparation containing 2.2 mg/ml CD38ecd-Fc-10H and incubated for 15 min at 37° C. As control experiment, 2 µl to 32 µl PBS, pH 7.4, instead of CD38ecd-Fc-10H was pipetted to the plasma.

Antibody Screening: 50 µl of Screen-Cyte 0.8% Cell #3, lot 17005 (Medion Grifols Diagnostics, Duedingen, Switzerland) and 25 µl of the plasma pretreated as above were pipetted in the incubation chamber of a microcolumn in a DG Gel Coombs Card (lot 17612.01 exp 2018-02; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the anti-CD38 present in the patient sample.

With 2 µl of CD38ecd-Fc10H-20170313-NTAEPCPBS, a 1:16 dilution of the plasma could be inhibited completely. With 32 µl of 2.2 mg/ml CD38ecd-Fc10H-20170313-NTAEPCPBS, the anti-CD38 in undiluted plasma could be inhibited completely.

Example 4b: Inhibition Using a Preparation Containing 35 mg/ml CD38ecd-Fc-10H

Sample preparation (inhibition test): 25 µl of anti-CD38 containing plasma of patient 2 (displaying an anti-CD38 titer of 1:4096) was incubated with 2 µl of 35 mg/ml CD38ecd-Fc-10H and incubated for 15 min at 37° C. As control experiment, 2 µl PBS, pH 7.4, instead of CD38ecd-Fc-10H was pipetted to the plasma.

Antibody Screening: 50 µl of each cell of Screen-Cyte 0.8%, lot 17017 (Medion Grifols Diagnostics, Duedingen, Switzerland) and 25 µl of the plasma pretreated as above were pipetted in the incubation chamber of a microcolumn in a DG Gel Coombs Card (lot 16681.01 exp 2017-11; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the anti-CD38 present in the patient sample.

With 2 µl of CD38ecd-Fc10H-20170915-PROTA, plasma from patient 2 could be inhibited completely.

Example 4c: Inhibition of Simulated DARA Patient Plasma (0.5 mg/ml) Using a Preparation Containing 33 mg/ml CD38ecd-Fc-10H Generation of simulated patient plasma with spiked DARA: Anti-CD38 therapeutic drug (Darzalex) was spiked in human AB plasma at a final concentration of 0.5 mg/ml.

Sample preparation (inhibition test): 25 µl of simulated DARA patient plasma was incubated with 2 µl of 33 mg/ml CD38ecd-Fc-10H and incubated for 15 min at 37° C. As control experiment, 2 µl PBS, pH 7.4, instead of CD38ecd-Fc-10H was pipetted to the plasma.

Antibody Screening: 50 µl of each cell of Screen-Cyte 0.8%, lot 180005 (Medion Grifols Diagnostics, Duedingen, Switzerland) and 25 µl of the simulated plasma pretreated as above were pipetted in the incubation chamber of a microcolumn in a DG Gel Coombs Card (lot 17133.01 exp 2018-10; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the anti-CD38 present in the patient sample.

With 2 µl of CD38ecd-FC10H-GDS20171106, a concentration of 0.5 mg/ml spiked into donor plasma could be inhibited completely.

Example 5—Inhibition of Anti-CD38 by CD38ecd-Fc-10H is Specific and does not Interfere with Underlying Blood Group Relevant Alloantibodies Example 5a: Detection of a Low Titer Anti-D in Simulated DARA Plasma after Pre-Treatment with 2.2 mg/ml CD38ecd-Fc-10H Simulated plasma of patient under Darzalex treatment was spiked with a human polyclonal Anti-D that became detectable by a commercial screening panel only after pre-treatment with sCD38. In simulated spiked plasma pretreated with PBS it was impossible to correctly detect the anti-D since Darzalex interfered with the antibody screening procedure, thus leading to positive reactions in all cells of the antibody screening assay derived from the reaction of the screening cells with Darzalex.

(1) Drug Titration Experiments: Anti-CD38 therapeutic drug (Darzalex; lot GHS0901, Janssen, USA) was used to prepare a simulated patient plasma after dilution in human AB plasma wherein the human AB plasma was spiked with a human anti-D polyclonal antibody. 75 µl of anti-CD38 therapeutic drug (Darzalex) was arithmetically titrated in human AB plasma to generate simulated patient plasma. 50 µl of Screen-Cyte 0.8% Cell #3, lot 17005 (Medion Grifols Diagnostics, Duedingen, Switzerland) and 25 µl of the each titer of Darzalex were pipetted in the incubation chamber of a microcolumn in a DG Gel Coombs Card (lot 17612.01 exp 2018-02; Diagnostic Grifols, Barcelona, Spain) and incubated for 15 min at 37° C. The Card was then centrifuged in a centrifuge for DG Gel cards and the results read. This experiment established the titer of anti-CD38 contained in Darzalex as 1:64,000.

(2) Anti-D titration: Donor serum with high-titer anti-D was arithmetically titrated in human AB plasma. 50 µl of Screen-Cyte 0.8% Cell #1, lot 17005 (Medion Grifols Diagnostics, Duedingen, Switzerland) and 25 µl of each titer of anti-D were pipetted in the incubation chamber of a microcolumn in a DG Gel Coombs Card (lot 17612.01 exp 2018-02; Diagnostic Grifols, Barcelona, Spain) and incubated for 15 min at 37° C. The Card was then centrifuged in a centrifuge for DG Gel cards and the results read. This experiment established the titer of anti-D in the donor serum as 1:16,000 with cell 1.

(3) Simulated patient plasma: A dilution of 1:512 of anti-D in human AB plasma was spiked with dilutions of 1:16,000 and 1:8,000 of Darzalex in order to achieve a simulated plasma with an anti-CD38 concentration that can be inhibited with 2 µl of 2.2 mg/ml CD38ecd-Fc-10H and to have anti-D close to the limit of detection. The simulated spiked plasma reacted positively with all 3 cells in the antibody screening performed as provided below in (5). Additionally, 100 µl of anti-CD38 containing plasma of patient 2 (TF1707/527) were spiked with dilution of 1:4000 of anti-D.

(4) Sample preparation (inhibition test): 25 µl of simulated spiked plasma prepared as described in (1) to (3) above were incubated respectively with 2 µl or 32 µl of 2.2 mg/ml CD38ecd-Fc-10H (CD38ecd-Fc10H-20170313-NTAE-PCPBS) and incubated for 15 min at 37° C. As control experiment, 2 µl or 32 µl PBS, pH 7.4, instead of CD38ecd-Fc-10H was pipetted to the plasma.

(5) Antibody Screening: 50 µl of Screen-Cyte 0.8% Cells #1-3, lot 17005 (Medion Grifols Diagnostics, Duedingen, Switzerland) and 25 µl of the plasma pretreated as above were pipetted in the incubation chamber of a microcolumn in a DG Gel Coombs Card (lot 17612.01 exp 2018-02; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the Anti-CD38 present in the patient sample.

Figure 13:
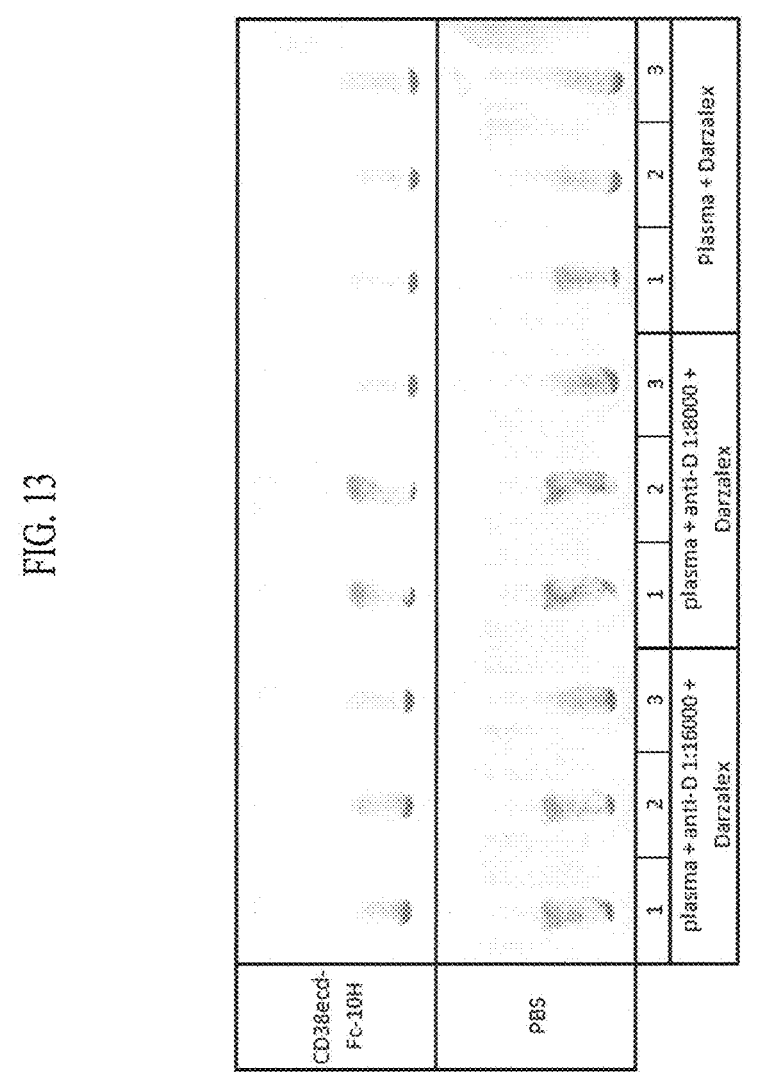

With 2 µl of 2.2 mg/ml CD38ecd-Fc10H-20170313-NTAEPCBS the simulated spiked plasma could be inhibited completely in the D negative cell #3 of the Antibody Screening Panel. With 32 µl of CD38ecd-Fc10H-20170313-NTAEPCBS, the spiked plasma of patient 2 could be inhibited completely in the Darzalex negative cell #3 of the Antibody Screening Panel (FIG. 13). Cells 1 and 2 remained positive after inhibition, indicating that the inhibition test performed as in (4) has no impact on the reactivity of the spiked anti-D antibody. The control experiments with not spiked simulated plasma (complete inhibition of cells #1-3 and with spiked plasma using PBS instead of CD38ecd-Fc-10H (no inhibition at all) showed the expected results (FIG. 13).

Example 5b: Inhibition of Anti-CD38 by CD38ecd-Fc-10H Allows for Detection of Relevant Unexpected Antibodies in Anti-CD38 Spiked Donor Plasma Anti-CD38 spiked donor plasma containing unexpected antibodies was used to evaluate detection of unexpected antibodies after complete inhibition of anti-CD38 by CD38ecd-Fc-10H. Anti-D, -E, -c, -Cw, -K, -Fya, -Jka, -S, -s, -M, -Lua, -Cob became detectable by a commercial screening panel only after pre-treatment with CD38ecd-Fc-10H.

(1) Generation of simulated patient plasma: donor AB plasma spiked with anti-CD38 and with alloantibodies: Anti-CD38 therapeutic drug (Darzalex) was spiked in human AB plasma at a final concentration of 0.5 mg/ml. Each alloantibody listed above was arithmetically titrated in human AB plasma: 50 µl of Screen-Cyte 0.8% (for each antibody a cell of the panel positive for the corresponding antigen was chosen based on product antigen matrix), and 25 µl of each dilution of the tested alloantibody were pipetted in the incubation chamber of a microcolumn in a DG Gel Coombs Card (lot 17133.01 exp 2018-10; Diagnostic Grifols, Barcelona, Spain) and incubated for 15 min at 37° C. The Card was then centrifuged in a centrifuge for DG Gel cards and the results read. The last dilution that gave a barely detectable positive reaction was used as dilution for spiking the unexpected antibody in anti-CD38-spiked donor plasma.

(2) Sample preparation (inhibition test): 25 µl of anti-CD38 spiked donor plasma containing unexpected antibodies were mixed with 2 µl of 33.4 mg/mL CD38ecd-Fc-10H and incubated for 15 min at 37° C.

(3) Antibody Screening: 50 µl of Screen-Cyte 0.8% Cells #1-3, lot 17026 or 18003 (Medion Grifols Diagnostics, Duedingen, Switzerland) and 25 µl of the pre-treated simulated plasma were pipetted in the incubation chamber of a microcolumn in a DG Gel Coombs Card (lot 17133.01 exp 2018-10; Diagnostic Grifols, Barcelona, Spain) and incubated for 15 min at 37° C. The Card was then centrifuged in a centrifuge for DG Gel cards and the results read.

Figure 14:
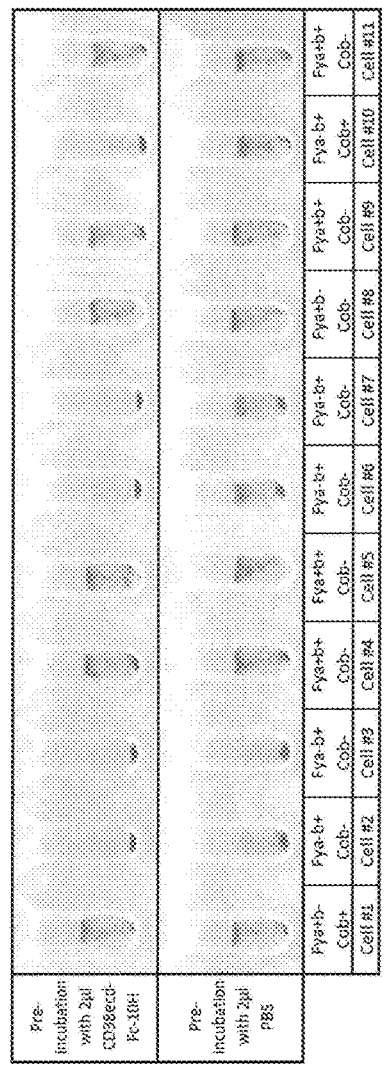
FIG. 14 shows data related to identification of barely detectable unexpected antibodies after inhibition of anti-CD38 by CD38ecd-Fc-10H.

A ratio of 2 µl of CD38ecd-Fc-10H (33.4 mg/ml) per 25 µl of plasma, allowed for detection of 16/16 underlying antibodies spiked at barely detectable amounts into DARA-spiked donor plasma (FIG. 14, Table 2). The antibody specificities included anti-D, -E, -c, -Cw, -K, -Fya, -Jka, -S, -s, -M, -Lua, -Cob.

TABLE 2

Detection of underlying antibodies in DARA-spiked donor plasma

| Specificity | Pre-incubation with 2 µl CD38ecd-Fc-10H | | |
|---|---|---|---|
| K | — | — | 1 |
| K | — | — | 1+ |
| D | 1 | 1 | — |
| D | +/− | 1 | — |
| E | — | 2 | — |
| E | — | 1 | — |
| Fya | — | — | 1 |
| Fya | — | — | 1 |
| Jka | 1 | — | 1− |
| s | — | +/− | — |
| S | — | — | 1− |
| c | — | 1− | 1− |

TABLE 2-continued

Detection of underlying antibodies
in DARA-spiked donor plasma

| Specificity | | Pre-incubation with 2 μl CD38ecd-Fc-10H | |
|---|---|---|---|
| Cob Fya | 2− | 1− | 2 |
| Lua | — | +/− | — |
| Cw | 1− | — | — |
| M | — | — | +/− |
| | Cell #1 | Cell #2 | Cell #3 |

Example 6—Stability Projection of CD38ecd-Fc-10H (Accelerated Stability)

Example 6a: Full Inhibition of Non-Diluted Anti-CD38 Plasma

Five aliquots of 100 μl of CD38ecd-Fc-10H preparation CD38ecd-Fc10H-20170313-NTAEPCPBS were aliquoted in separate tubes closed with screw caps and placed in an incubator at a constant temperature of 37° C. Before starting the incubation (i.e., day 0) and at days 7, 14, 21, and 31, one tube was transferred at 2-8° C. until day 31. At day 31 all aliquots were tested according to the following procedure:

Sample preparation (inhibition test): 25 μl of non-diluted anti-CD38 containing plasma of patient 1 (TF1715-197) was incubated with 32 μl of CD38ecd-Fc-10H and incubated for 15 min at 37° C. As control experiment, 32 μl PBS, pH 7.4, instead of CD38ecd-Fc-10H was pipetted to the plasma. Alternatively, plasma alone was incubated for 15 min at 37° C.

Antibody Screening: 50 μl of 1% dilution of a blood group O red blood cell in DG Gel Sol (lot 16015 exp 2018-04; Diagnostic Grifols, Barcelona, Spain) and 25 μl of the plasma pretreated as above were pipetted in the incubation chamber of a microcolumn in a DG Gel Coombs Card (lot 17612.01 exp 2018-02; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the anti-CD38 present in the patient sample. The results of days 0, 7, 14, 21, and 31 equally showed complete inhibition, whereas the control experiments showed a reaction score of 2, i.e., no inhibition. Based on an Arrhenius plot, the demonstrated stability of the CD38ecd-Fc-10H of 31 days at 37° C. can be translated into a stability of at least 24 months, when stored at 2 to 8° C.

Example 6b: Inhibition of Titrated Anti-CD38 Plasma by 2 μl of 2.2 mg/ml CD38ecd-Fc-10H Five aliquots of 100 μl of CD38ecd-Fc-10H preparation CD38ecd-Fc10H-20170313-NTAEPCPBS were aliquoted in separate tubes closed with screw caps and put in an incubator at a constant T of 37° C. Before starting the incubation and at days 7, 14, 21, 31 one tube was transferred at 2-8° until day 31. At day 31 all aliquots were tested according to the following procedure: 200 μl of anti-CD38 containing plasma of patient 1 (TF1715-197) was arithmetically titrated in in PBS, pH 7.4 (1:2, 1:4, 1:8, 1:16) after it had been established in preliminary experiments that 25 μl of plasma diluted 1:8 could be fully inhibited with a volume of 2 μl of CD38ecd-Fc-10H.

Sample preparation (inhibition test): 25 μl of the respective titration of Anti-CD38 containing plasma of patient 1 TF1715-197) was incubated with 2 μl of 2.2 mg/ml CD38ecd-Fc-10H and incubated for 15 min at 37° C. As control experiment, 2 μl PBS, pH 7.4, instead of CD38ecd-Fc-10H was pipetted to the plasma.

Antibody Screening: 50 μl of 1% dilution of a blood group O red blood cell in DG Gel Sol (lot 16015 exp 2018-04; Diagnostic Grifols, Barcelona, Spain) and 25 μl of the plasma pretreated as above were pipetted in the incubation chamber of a microcolumn in a DG Gel Coombs Card (lot 17612.01 exp 2018-02; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the Anti-CD38 present in the patient sample. The results of days 0, 7, 14, 21, and 31 equally showed complete inhibition at titer 1:8, whereas the control showed a reaction score of 2, i.e., no inhibition, throughout the whole titration. Based on an Arrhenius plot, the demonstrated stability of the CD38ecd-Fc-10H of 31 days at 37° C. can be translated into a stability of at least 24 months, when stored at 2 to 8° C.

Example 7—Functionality Comparison of CD38ecd-Fc-10H Vs Recombinant Human CD38 (rhCD38)

Generation of simulated patient plasma with spiked DARA: Anti-CD38 therapeutic drug (Darzalex) was spiked in human AB plasma at a final concentration of 0.5 mg/ml.

Sample preparation (inhibition test): 25 μl of anti-CD38 spiked donor plasma were mixed with 2 μl of 33.4 mg/mL CD38ecd-Fc10H or with 0.447 mg/ml of rhCD38 (CD38-6H, R&D Systems, cat #2404-AC-010, lot. PEH0417081, Minneapolis, USA) or with PBS, pH 7.4 and incubated for 15 min at 37° C.

Antibody Screening: 50 μl of Screen-Cyte 0.8% Cells #1-3, lot 18001 (Medion Grifols Diagnostics, Duedingen, Switzerland) and 25 μl of the pre-treated simulated plasma were pipetted in the incubation chamber of a microcolumn in a DG Gel Coombs Card (lot 17108.01 exp 2018-09; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the Anti-CD38 present in the patient sample.

Figure 15:
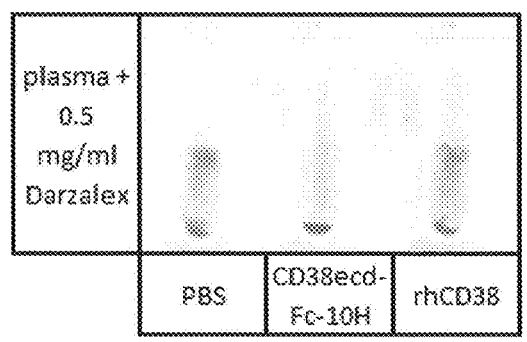
FIG. 15 shows data related to inhibition of anti-CD38 by CD38ecd-Fc-10H or rhCD38.

2 μl of recombinant CD38ecd-Fc10H allowed for complete inhibition of 0.5 mg/ml anti-CD38. In contrast, commercial rhCD38 used in the same experimental settings, could not inhibit the same anti-CD38 load (FIG. 15).

Example 8—Comparison of Incubation Times and Incubation Temperatures for Inhibition of Anti-CD38 by CD38ecd-Fc10H Sample preparation (inhibition test): Anti-CD38 therapeutic drug (Darzalex; lot GHS0901, Janssen, USA) was diluted in BPS ph 7.4 at a final concentration of 2 mg/ml. 150 μl of this solution were arithmetically titrated in PBS, pH 7.4 until 1:8. 25 μl of each anti-CD38 dilution were mixed with 2 μl 33.4 mg/mL CD38ecd-Fc10H, and incubated for 15 minutes at 37° C., 15 minutes at room temperature, or 30 min at room temperature.

Antibody Screening: 50 µl of Screen-Cyte 0.8% Cells #3, lot 17025 (Medion Grifols Diagnostics, Duedingen, Switzerland) and 25 µl of the above pre-treated sample were pipetted in the incubation chamber of a microcolumn in a DG Gel Coombs Card (lot 17108.01 exp 2018-09; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the Anti-CD38 present in the patient sample.

Figure 16:
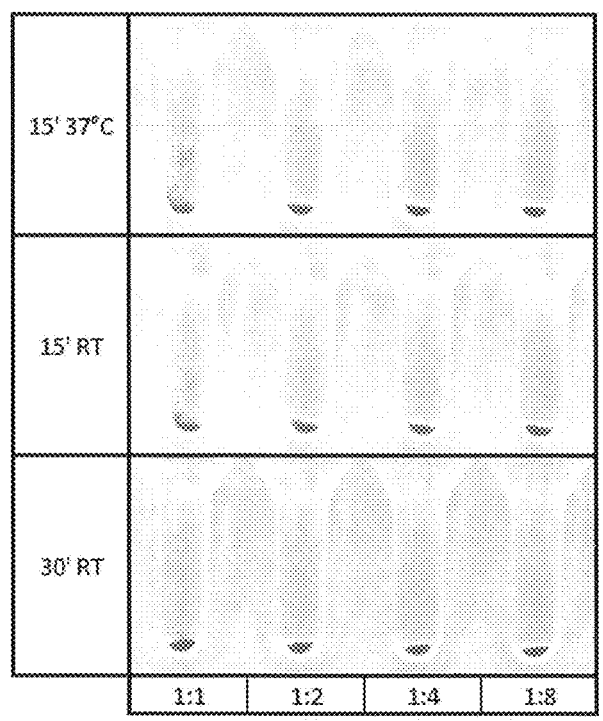
FIG. 16 shows equivalent functionality of pre-treatments with CD38ecd-Fc-10H at different temperatures and incubation times.

With 2 µl of CD38ecd-Fc10H, a 1:4 dilution of the sample (corresponding to 0.5 mg/ml anti-CD38) could be inhibited completely in all three pre-treatments (FIG. 16).

Example 9—Activity Comparison of CD38ecd-Fc-10H Vs CD38ecd-Flex-Fc-10H Vs CD38ecd-10H Sample preparation (inhibition test): Anti-CD38 therapeutic drug (Darzalex; lot GHS0901, Janssen, USA) was diluted in BPS ph 7.4 at a final concentration of 1 mg/ml. 150 µl of this solution were arithmetically titrated in PBS, pH 7.4 until 1:8. 25 µl of each anti-CD38 dilution were mixed with 2 µl 8.5 mg/ml CD38ecd-Fc-10H, or 8.5 mg/ml CD38ecd-flex-Fc-10H, or 5 mg/ml CD38ecd-10H and incubated for 15 minutes at 37° C.

Antibody Screening: 50 µl of Screen-Cyte 0.8% Cells #3, lot 18009 (Medion Grifols Diagnostics, Duedingen, Switzerland) and 25 µl of the above pre-treated sample were pipetted in the incubation chamber of a microcolumn in a DG Gel Coombs Card (lot 17133.01 exp 2018-10; Diagnostic Grifols, Barcelona, Spain) and incubated for 15 min at 37° C. The Card was then centrifuged in a centrifuge for DG Gel cards and the results read. A completely negative result (a flat button of cells at the bottom of the microcolumn) was indicative of a complete inhibition of the Anti-CD38 present in the patient sample.

Figure 17:
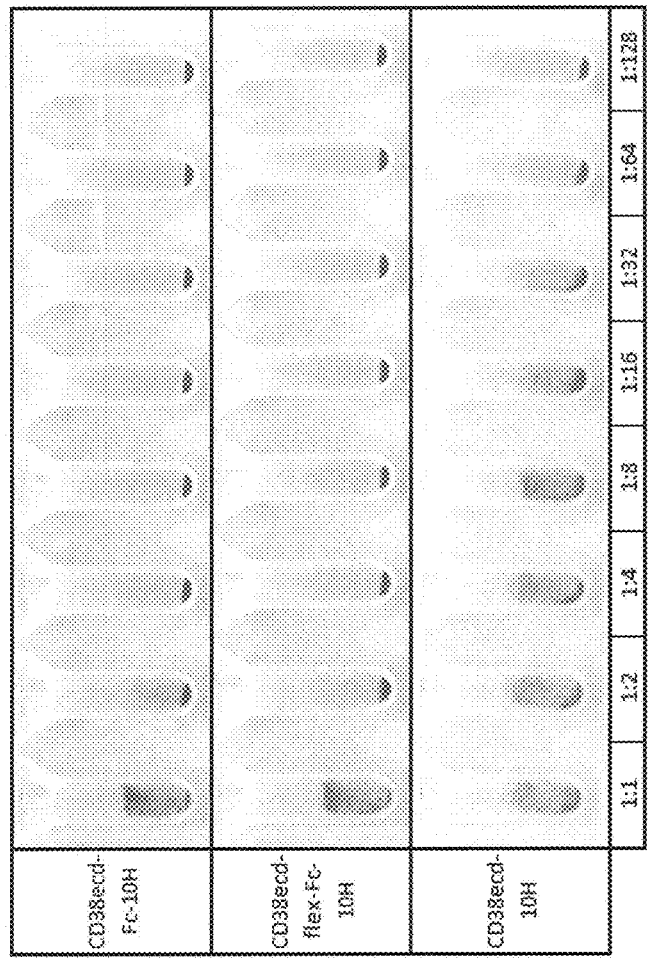
FIG. 17 shows better functionality of CD38ecd-Fc-10H and CD38ecd-flex-Fc-10H versus CD38ecd-10H.

With 2 µl of CD38ecd-Fc-10H and with 2 µl of CD38ecd-flex-Fc-10H, a 1:8 dilution of the sample (corresponding to 0.125 mg/ml anti-CD38) could be inhibited completely. With 2 µl of CD38ecd-10H a 1:8 dilution of the sample could not be inhibited completely. Only a 1:128 dilution of the sample (corresponding to 0.008 mg/ml anti-CD38) could be completely inhibited with 2 µl of CD38ecd-10H (FIG. 17).

Example 10—Oligomerization of Fc-PolyHis Fusion Proteins

Three protein of interest, CD38ecd, CD47ecd1 and Gp1bα, were recombinantly fused to different versions of the Fc-polyHis oligomerization tag in order to investigate the ability to form oligomers of the resulting recombinant fusion proteins.

One version was the recombinant sCD38 protein fused to a Fc-10His tag. This protein was expressed and purified up to 50 mg/ml without detection of visible aggregation. In a second version, the recombinant sCD38 protein was fused to a flex-Fc-10His tag. In this version of the fusion protein the hinge region of Fc, was replaced by a flexible linker without cysteines. In a third version, the recombinant sCD38 protein was fuses to a Fc region. In a fourth version, the recombinant sCD38 protein was fused to a 10His tag.

In the aim to apply the method for oligomerization of fusion proteins to other proteins of interest, the oligomerization tag Fc-10His was fused to the CD47ecd1 protein in one version of this protein. A different version of the oligomerization tag was also fused to a Gp1bα protein. In a first version the recombinant Gp1bα protein was fused to a Fc-8His tag. In a second version, the recombinant Gp1bα protein was fused to a 6His tag. In a third version the recombinant Gp1bα protein was fused to a SBP-6H tag. In a forth version the recombinant Gp1bα protein was fused to was fused to a p53-6His tag. The tags Fc-10His and Flex-Fc-10His on their own were also used as controls.

The multiple versions of the fusion proteins were expressed and purified in an eukaryotic expression system. By Size Exclusion Chromatography Dynamic Light Scattering (SEC-MALS/DLS) the mass (Mw), the hydrodynamic radius (Rh(w)) and the polydispersity (Mw/Mn) of the proteins in solution was measured (Table 3). The degree of oligomerization was calculated from the ratio between the measured mass (Mw) and the theoretical mass (Th·Mw).

For sCD38 fusion proteins the ability of the protein to titrate an antibody as in the anti-CD38 (DARATUMUMAB) inhibition IAT was also tested using CD38ecd-Fc-10H as reference.

TABLE 3

Degree of oligomerization of recombinant fusion proteins

| Recombinant protein | Th. Mw (kDa) | Mw (kDa) | Mw/ Th.Mw | Polydispersity Mw/Mn | Rh*(w) (nm) | Oligomer degree | Functionality |
|---|---|---|---|---|---|---|---|
| CD38ecd-Fc-10H | 57 | 668.9 (0.1%) | 11.7 | 1.002 (0.2%) | 9.8 (7%) | 12 mer | 100% |
| CD38ecd-flex-Fc-10H | 57 | 700.8 (0.6%) | 12.3 | 1.002 (0.8%) | 9.6 (6%) | 12 mer | 100% |
| CD38ecd-Fc | 56 | 113.7 (0.8%) | 2.3 | 1.009 (1%) | <9 | 2 mer | 50% |
| CD38ecd-10H | 31 | 35.6 (3%) | 1.2 | 1.000 (4%) | <9 | 1 mer | 12.5% |
| CD47ecd1-Fc-10H | 41 | 513.3 (0.9%) | 12.5 | 1.005 (1%) | 9.3 (28%) | 12 mer | nd |
| Gp1bα-Fc-G-8H + 10 mM EDTA | 59 | 144 (1.842%) | 2.4 | 1.012 (2.6%) | <9 | 2 mer | N/A |
| Gp1bα-Fc-G-8H No EDTA treatment | 59 | 773 (1.5%) | 13 | 1.06 (2.34%) | 9.10 (44%) | 12 mer | N/A |

TABLE 3-continued

Degree of oligomerization of recombinant fusion proteins

| Recombinant protein | Th. Mw (kDa) | Mw (kDa) | Mw/Th.Mw | Polydispersity Mw/Mn | Rh*(w) (nm) | Oligomer degree | Functionality |
|---|---|---|---|---|---|---|---|
| Gp1bα-6H | 33 | 36.23 (3%) | 1.1 | 1.016 (3.75%) | <9 | 1 mer | N/A |
| Gp1bα-SBP-6H | 37 | 41.77 (0.6%) | 1.12 | 1.003 (0.88%) | <9 | 1 mer | N/A |
| Gp1bα-p53-6H | 37 | 146 (1.081%) | 3.94 | 1.006 (1.57%) | <9 | 4 mer | N/A |
| Fc-10H | 30 | 393.6 (2%) | 13.12 | 1.072 (3%) | <9 | 12 mer | 0% |
| flex-Fc-10H | 30 | 303.5 (2%) | 10.1 | 1.021 (3%) | <9 | 10 mer | 0% |

*The Rh(w) of molecules smaller than 9 nm is unreliable.

Oligomerization tags comprising the specific combination of a Fc region and poly-His domain (Fc-polyHis) triggers the oligomerization (at least 12mer or 6mer of dimers) of at least 3 proteins of interest (sCD38, CD47ecd1 and Gp1bα) fused to it at the N-terminus. The Fc-10His tag itself without a protein of interest fused to also form oligomers. The data shown in Table 3 strongly indicate that the oligomerization is an intrinsic property of Fc-polyHis tags which is not connected to the protein of interest used. Oligomerization of the protein of interest is snot dependent on the hinge region of Fc, as proteins fused to the Flex-Fc-10His also shows oligomerization. Proteins fusions comprising only a polyHis tag without the Fc region does not trigger any oligomerization and the proteins obtained are monomers as expected. All the proteins fusion comprising a oligomerization tag Fc-polyHis are highly monodisperse indicating that they are not aggregates of unfolded molecules.

Finally, the fusion of a Fc-polyHis oligomerization tag to sCD38 proteins increases the avidity of CD38ecd in titrating an anti-CD38

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

All references cited in this disclosure are incorporated herein by reference in their entireties.

The invention claimed is:

1. A composition for binding to an anti-CD38 antibody, the composition comprising a recombinant polypeptide that interferes with a binding activity of an anti-CD38 antibody, wherein a sequence of the polypeptide comprises SEQ ID NO: 7 or SEQ ID NO: 12.

2. The composition of claim 1, wherein the anti-CD38 antibody is against human CD38, non-human CD38, or a combination thereof.

3. The composition of claim 1, wherein the anti-CD38 antibody is monoclonal, polyclonal, or a combination thereof.

4. The composition of claim 1, wherein the anti-CD38 antibody is selected from the group consisting of Daratumumb, isatuximab, and MOR202.

5. The composition of claim 1, wherein the recombinant polypeptide is expressed in a eukaryotic expression system.

6. The composition of claim 1, wherein the concentration of the recombinant polypeptide ranges from about 1 mg/ml to about 400 mg/ml.

7. A kit for bio-monitoring research and diagnostic assays, comprising the composition according to claim 1, a plate and reagents for identifying the presence of anti-CD38 antibodies.

8. The kit of claim 7, wherein the plate and reagents of the kit are configured for an ELISA assay.

9. A method of neutralizing or blocking binding of an anti-CD38 antibody in a sample, the method comprising:
providing a volume of the sample comprising the anti-CD38 antibody; and
incubating with a volume of the composition according to claim 1 sufficient to neutralize the anti-CD38 antibody in the sample.

10. The method of claim 9, wherein the sample is selected from the group consisting of blood, plasma, and serum.

11. The method of claim 9, wherein the anti-CD38 antibody is selected from the group consisting of Daratumumb, isatuximab, and MOR202.

12. The method of claim 9, wherein the volume of the sample ranges from about 25 µl to about 250 µl.

13. The method of claim 9, wherein the volume of the composition ranges from about 0.5 µl to about 50 µl.

14. The method of claim 9, wherein the concentration of the anti-CD38 antibody in the sample ranges from about 0.005 µg/ml to about 2000 µg/ml.

15. The method of claim 9, wherein the concentration of the recombinant polypeptide in the composition ranges from about 1 mg/ml to about 400 mg/ml.

16. The method of claim 9, wherein the neutralizing effect of the recombinant polypeptide ranges from about 70% to about 100%.

17. The method of claim 9, wherein the binding activity of anti-CD38 antibody is selected from the group consisting of interference with blood pre-transfusion testing, interference with blood compatibility testing, and interference with antibody therapy.

18. A method for delivering a unit of blood to a patient treated with anti-CD38 antibodies, the method comprising:
obtaining a sample from the patient, said sample being blood or a plasma and/or serum;
neutralizing the anti-CD38 antibodies in the sample according to the method of claim 9;
testing the sample for compatibility with the unit of blood;
selecting the unit of blood that is compatible with the sample based on the testing; and
delivering the selected unit of blood to the patient.

19. A method for removing anti-CD38 in human plasma, serum and/or blood during treatment of the plasma, serum, and/or blood, comprising exposing the plasma, serum, and/or blood to the composition of claim 1, wherein the recombinant polypeptide is tagged with an affinity tag.

20. The method of claim 19, wherein the treatment comprises a treatment selected from the group consisting of hemodialysis, peritoneal dialysis, hemofiltration, hemodiafiltration, plasma exchange therapy, and plasmapheresis.

21. The method of claim 19, wherein the affinity tag is selected from the group consisting of Glutathione S-Transferase (GST), small ubiquitin-like modifiers (SUMO), Avi-Tag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, SnoopTag, Biotin Carboxyl Carrier Protein (BCCP), Glutathione-S-transferase-tag, Green fluorescent protein-tag, other fluorescent protein tags, HaloTag, Maltose binding protein-tag, Nus-tag, Thioredoxin-tag, Fc-tag, Designed Intrinsically Disordered tags containing disorder promoting amino acids, and Ty tag.

22. A fusion protein comprising a sequence of SEQ ID NO: 7 or SEQ ID NO: 12.

23. The fusion protein of claim 22 further comprising a oligomerization tag is configured to form higher order of dimers up to 12mer or a hexamer of 2mer.

24. The composition of claim 1, wherein the concentration of the recombinant peptide is 35 mg/ml.

* * * * *

UNITED STATES PATENT AND TRADEMARK OFFICE
CERTIFICATE OF CORRECTION

PATENT NO. : 11,708,418 B2
APPLICATION NO. : 16/079068
DATED : July 25, 2023
INVENTOR(S) : Vincenzo Favaloro et al.

It is certified that error appears in the above-identified patent and that said Letters Patent is hereby corrected as shown below:

In the Specification

In Column 2, Lines 35-36, delete "application" and insert --application.--.

In Column 10, Line 11, delete "phage" and insert --phage,--.

In Column 10, Line 42, before "histidine" insert --10--.

In Column 11, Line 29, delete "GranzymeB," and insert --Granzyme B,--.

In Column 11, Line 29, delete "Iodosobenzoic" and insert --Iodoxybenzoic--.

In Column 17, Line 34, delete "oligomeriation" and insert --oligomerization--.

In Column 23, Line 64, delete "in in" and insert --in--.

In Column 24, Line 62, delete "ph" and insert --pH--.

In Column 25, Line 23, delete "ph" and insert --pH--.

In Column 25, Line 26, delete "8.5" and insert --~8.5--.

In Column 25, Line 26, delete "8.5" and insert --~8.5--.

In Column 25, Line 27, delete "5" and insert --~5--.

In Column 27, Line 28 (Approx.), delete "snot" and insert --not--.

In Column 27, Line 38 (Approx.), delete "anti-CD38" and insert --anti-CD38.--.

Signed and Sealed this
Second Day of January, 2024

*Katherine Kelly Vidal*
Katherine Kelly Vidal
*Director of the United States Patent and Trademark Office*

CERTIFICATE OF CORRECTION (continued)
U.S. Pat. No. 11,708,418 B2

In the Claims

In Column 77, Claim 4, Lines 29-30 (Approx.), delete "Daratumumb," and insert --Daratumumab,--.

In Column 77, Claim 11, Line 51 (Approx.), delete "Daratumumb," and insert --Daratumumab,--.